US010891719B2

(12) United States Patent
Srivastava et al.

(10) Patent No.: US 10,891,719 B2
(45) Date of Patent: Jan. 12, 2021

(54) SYSTEMS, METHODS AND PROGRAMS FOR DENOISING SIGNALS USING WAVELETS

(71) Applicant: CORNELL UNIVERSITY, Ithaca, NY (US)

(72) Inventors: Madhur Srivastava, Ithaca, NY (US); Jack H. Freed, Ithaca, NY (US); C. Lindsay Anderson, Ithaca, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 0 days.

(21) Appl. No.: 16/301,209

(22) PCT Filed: May 11, 2017

(86) PCT No.: PCT/US2017/032174
§ 371 (c)(1),
(2) Date: Nov. 13, 2018

(87) PCT Pub. No.: WO2017/197123
PCT Pub. Date: Nov. 16, 2017

(65) Prior Publication Data
US 2019/0287220 A1    Sep. 19, 2019

Related U.S. Application Data

(60) Provisional application No. 62/334,626, filed on May 11, 2016.

(51) Int. Cl.
*G06T 5/00* (2006.01)
*A61B 5/00* (2006.01)
(Continued)

(52) U.S. Cl.
CPC ............ *G06T 5/002* (2013.01); *A61B 5/7203* (2013.01); *A61B 5/726* (2013.01); *G06F 17/148* (2013.01);
(Continued)

(58) Field of Classification Search
CPC . G06T 5/002; G06T 5/10; G06T 2207/20016; G06T 2207/20064;
(Continued)

(56) References Cited

U.S. PATENT DOCUMENTS

| | | | |
|---|---|---|---|
| 6,879,729 B2* | 4/2005 | Kamath | .................... G06K 9/40 382/254 |
| 7,515,763 B1* | 4/2009 | Zhong | ...................... G06K 9/40 382/240 |

(Continued)

OTHER PUBLICATIONS

Wang, Z. et al., "Study on an Improved Wavelet Shift-Invariant Threshold Denoising for Pulsed Laser Induced Glucose Photoacoustic Signals", Visual Communications and Image Processing; Oct. 2015; pp. 967407-1 to 967407-11, vol. 9674.
(Continued)

*Primary Examiner* — Phuoc Tran
(74) *Attorney, Agent, or Firm* — Scully Scott Murphy & Presser

(57) ABSTRACT

Methods, systems and programs for denoising a signal using discrete wavelet transformation are provided. For example, a method for denoising a signal may include determining a number of resolution levels to denoise, determining variable threshold(s) for each resolution level, applying the determined variable threshold(s) to denoise at least a detail component of each of the determined resolution levels. Each variable threshold includes a separately determined lower threshold and upper threshold. The method for denoising a signal may further include transforming, using an inverse
(Continued)

discrete wavelet transformation, at least the denoised detail component for each of the determined resolution levels into a denoised signal.

30 Claims, 19 Drawing Sheets

(51) Int. Cl.
*G06F 17/14* (2006.01)
*G06T 5/10* (2006.01)

(52) U.S. Cl.
CPC ...... *G06T 5/10* (2013.01); *G06T 2207/20016* (2013.01); *G06T 2207/20064* (2013.01)

(58) Field of Classification Search
CPC ... G06T 2200/24; G06F 17/148; A61B 5/726; A61B 5/7203
See application file for complete search history.

(56) References Cited

U.S. PATENT DOCUMENTS

| | | | | |
|---|---|---|---|---|
| 2005/0107962 | A1* | 5/2005 | Zhan | G05B 23/0221 702/35 |
| 2011/0191047 | A1* | 8/2011 | Pupalaikis | G06F 19/00 702/69 |
| 2012/0215453 | A1* | 8/2012 | Poole | G01V 1/364 702/16 |
| 2013/0182533 | A1* | 7/2013 | Rentsch-Smith | G01V 1/38 367/24 |
| 2016/0161621 | A1* | 6/2016 | Salama | G01V 1/364 702/17 |

OTHER PUBLICATIONS

Ren, Z. et al., "Research of the bio-chemical spectrum denoise based on a novel wavelet threshold function and an improved translation-invariance method", Proc. of SPIE, 2009, pp. 72801Q-1 to 72801Q-12.

Chang, S.G. et al., "Adaptive Wavelet Thresholding for Image Denoising and Compression", IEEE Transactions on Image Processing, Sep. 2000, pp. 1532-1546, vol. 9, No. 9.

Extended European Search Report dated Nov. 27, 2019 issued in European Application No. 17796847.6.

Donoho, D. et al., "Ideal Spatial Adaptation by Wavelet Shrinkage" Biometrika, 1994, pp. 425-455, vol. 81, No. 3.

Donoho, D., "De-noising by Soft-Thresholding", IEEE Transactions on Information Theory, May 1995, pp. 613-627, vol. 41, No. 3.

Johnstone, I. et al., "Wavelet Threshold Estimators for Data with Correlated Noise", J. Roy. Statist. Soc. B, 1997, pp. 319-351, vol. 59, No. 2.

Donoho, D. et al., "Adapting to Unknown Smoothness via Wavelet Shrinkage", Journal of the American Statistical Association, 1995, pp. 1200-1224, vol. 90, No. 432.

Cohen, R., "Signal Denoising Using Wavelets," Technion, 2012, pp. 1-27.

Fodor, I. et al., "Denoising through wavelet shrinkage: an empirical study", Journal of Electronic Imaging, Jan. 2003, pp. 1200-1224, vol. 12, No. 1.

Zhao, R. et al., "Improved Threshold Denoising Method Based on Wavelet Transform", 7th International Conference on Modelling, Identification and Control, 2015, pp. 1-4.

Poornachandra, S. et al., "WaveShrink Using Modified Hyper-Shrinkage Function", Engineering in Medicine and Biology 27th Annual Conference, 2005, pp. 30-32.

Lin, Y. et al., "A New Threshold Function for Signal Denoising Based on Wavelet Transform", International Conference on Measuring Technology and Mechatronics Automation, 2010, pp. 200-203.

* cited by examiner

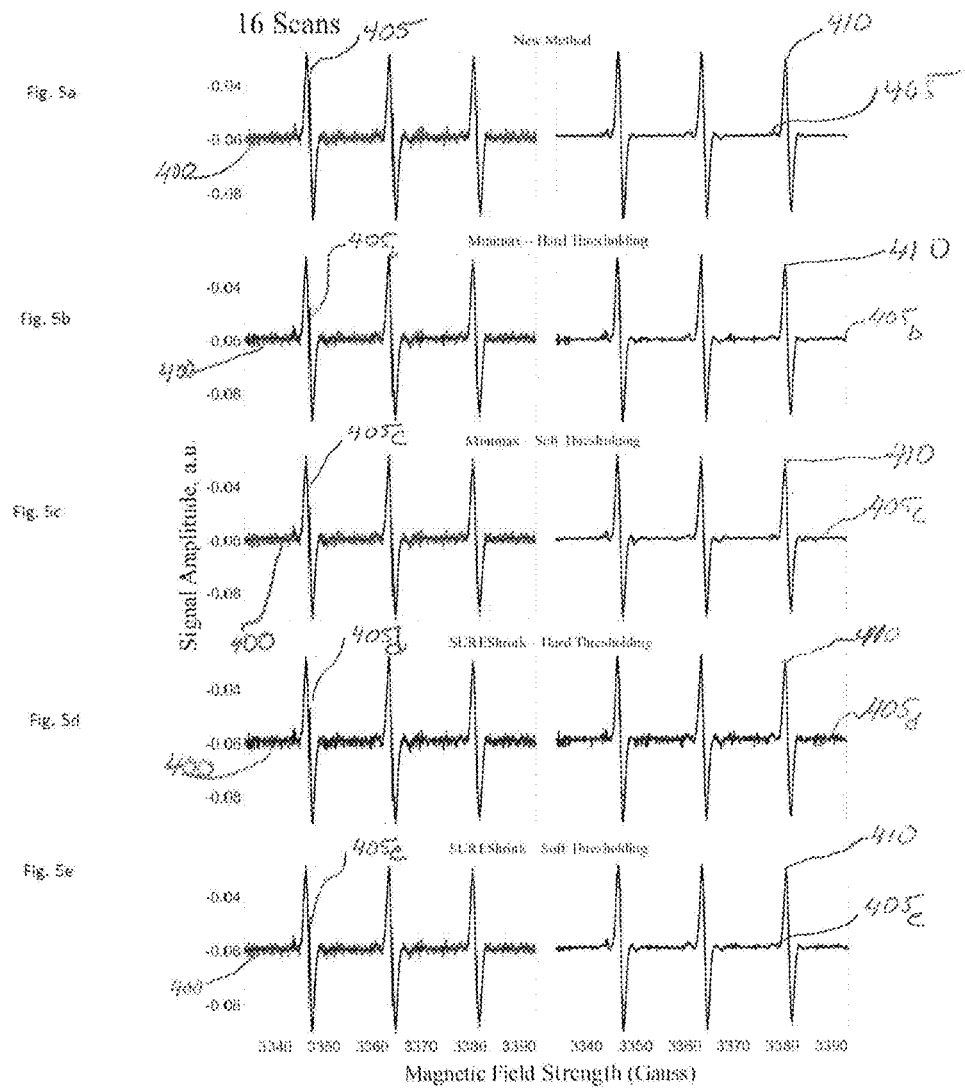

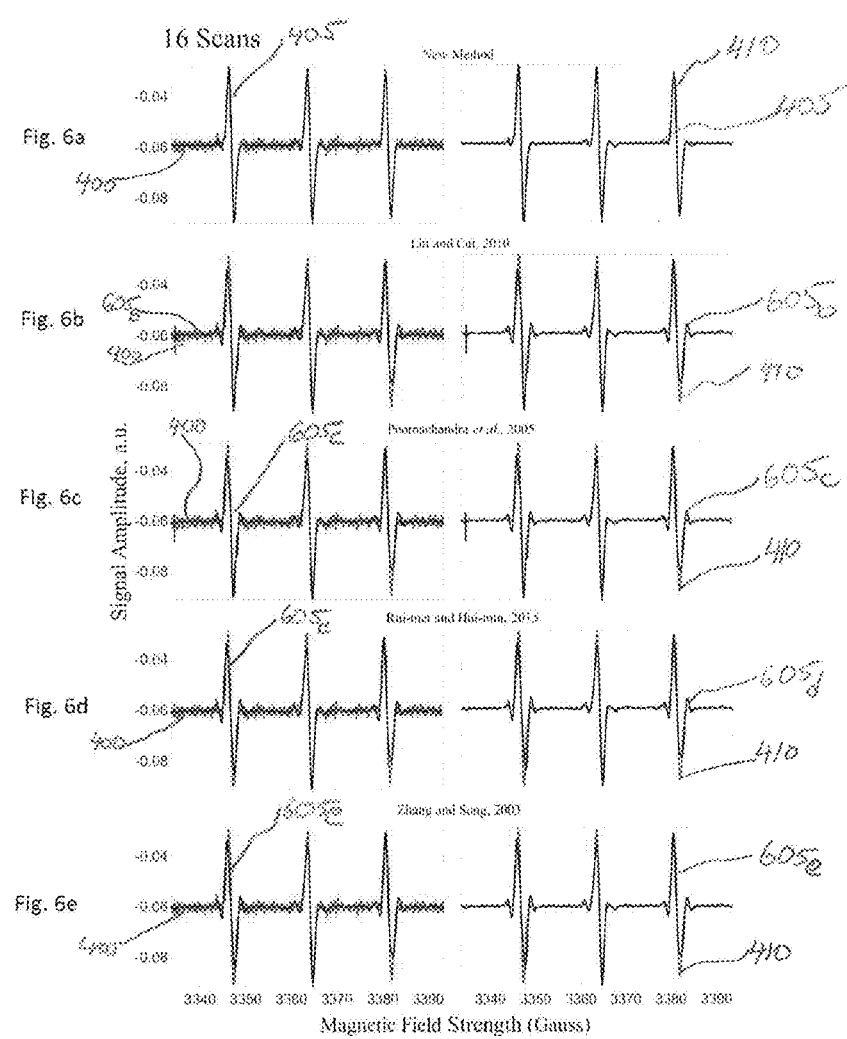

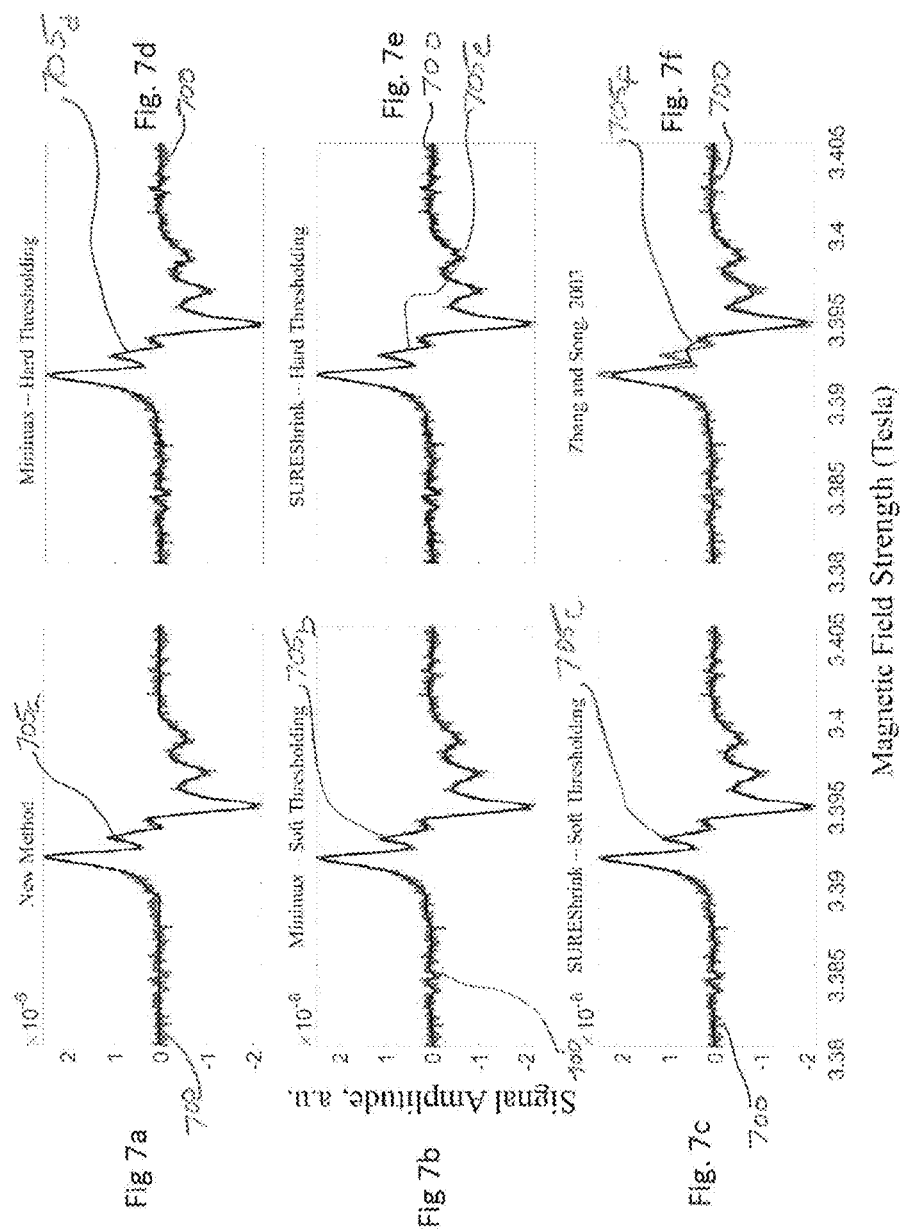

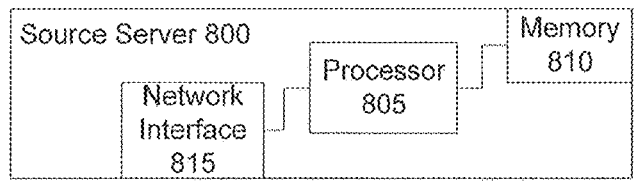
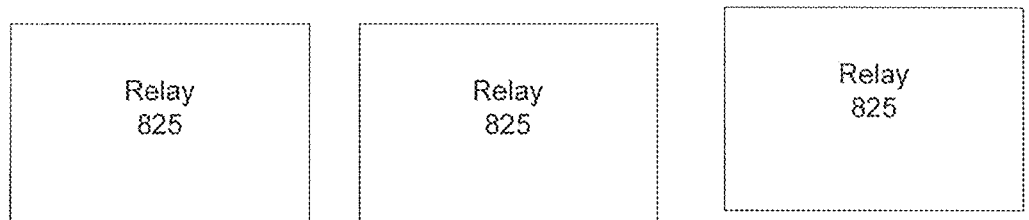
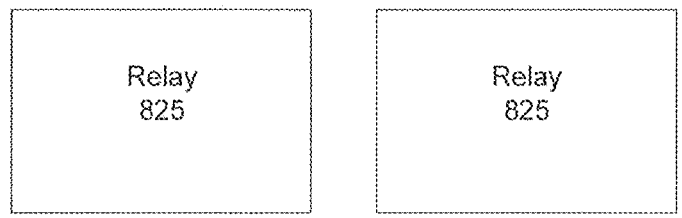
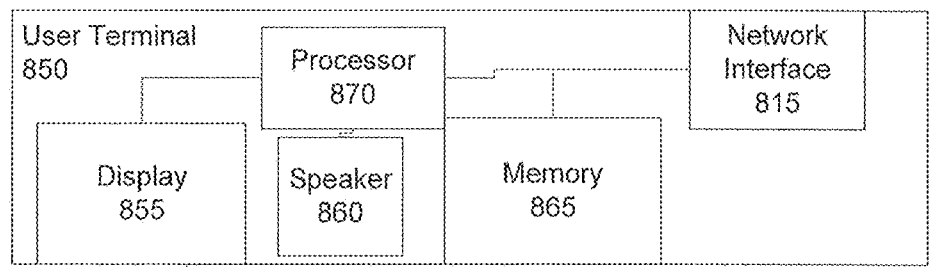
Fig. 8

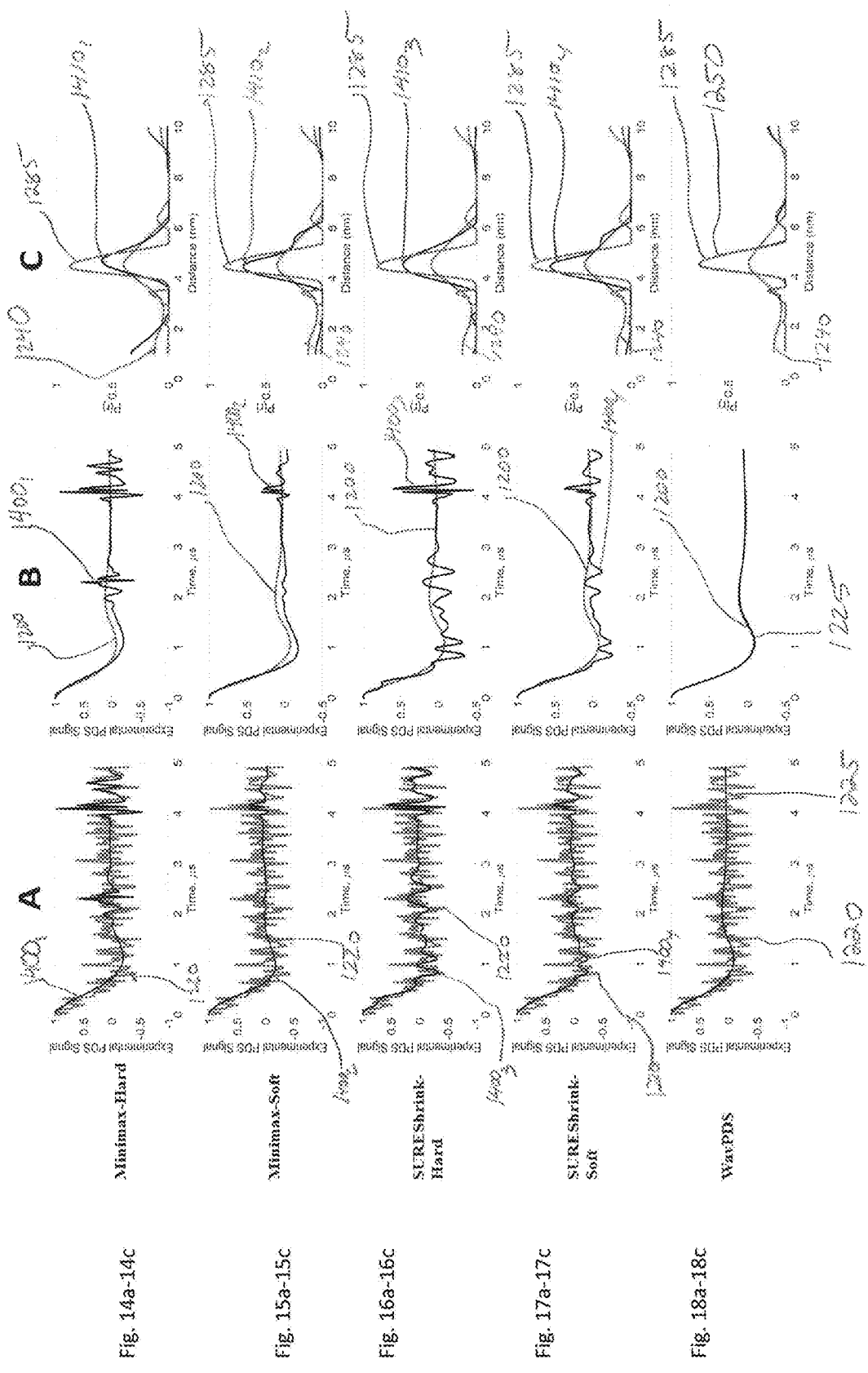

2500

SYSTEMS, METHODS AND PROGRAMS FOR DENOISING SIGNALS USING WAVELETS

CROSS-REFERENCE TO RELATED APPLICATIONS

This application claims the benefit of and priority to U.S. Provisional Application Ser. No. 62/334,626 filed on May 11, 2016, the contents of which is incorporated herein by reference.

STATEMENT REGARDING FEDERALLY SPONSORED RESEARCH AND DEVELOPMENT

This invention was made with government support under contract no. GM103521 awarded by the National Institutes of Health. The government has certain rights in the invention.

BACKGROUND

Noise is generally unwanted components of a signal that can arise from acquisition, storing, transmission and processing. Noise is typically a natural result of electronic circuits and signal cables.

Noise in signals can cause many problems. For example, noise can cause an inaccurate representation or determination of the data in the signal or no determination at all. Where data is being transmitted from a remote location, noise can cause download gaps or interruptions. This results in either an increase in download time (which increases the bandwidth needed for transmission) and/or missing data. Noise also may have different impact on different types of signals. For example, when the signal contains audio and the audio is listened to, the noise in the audio may be audible in the form of buzzing, whereas when the signal contains video, the noise in the video may be visually seen on a display in the form of pixels, bars, or strips being incorrect or blank.

Several techniques have been developed to attempt to eliminate or reduce the noise in a signal. Many of these techniques have potential side effects, are too time consuming for real-time analysis or do not result in an effective denoising of the signal. For example, certain techniques use filters to smooth the noisy signal. However, a major drawback of filtering (and estimators) is that the signal can be distorted. It can morph the signal which may or may not result in the original signal.

SUMMARY

Accordingly, disclosed is a method of denoising a signal. The method comprises transforming a signal using a discrete wavelet transformation into a first wavelet component and a second wavelet component for each of a plurality of different resolutions, respectively, using preset wavelets. Each of the first wavelet component and the second wavelet component has a plurality of coefficients. The method further comprises determining a number of different resolutions, where the number is k, of the plurality of different resolutions for use in thresholding by examining at least coefficients for the first wavelet component for at least two of the plurality of different resolutions, respectively, for each of the determined number of different resolutions for use in thresholding, comparing each coefficient in the first wavelet component with a variable threshold, and selectively changing a value of the coefficient based on the comparison thereby generating a modified first wavelet component having changed coefficients and unchanged coefficients. The variable threshold for each of the determined number of different resolutions is different. The method further comprises, for the kth different resolution, comparing each coefficient in the second wavelet component with a second variable threshold, and selectively changing a value of the coefficient based on the comparison, thereby generating a modified second wavelet component having changed coefficients and unchanged coefficients. The method further comprises transforming, using an inverse discrete wavelet transformation, the modified first wavelet component for each of the determined number of resolutions and the modified second wavelet component into a denoised signal.

Also disclosed is a method of denoising a signal comprising reversing in time, a signal and transforming the time reversed signal using a discrete wavelet transformation into a first wavelet component for each of a number of different resolutions, wherein the number of different resolutions is k and a second wavelet component for the kth different resolution. Each of the first wavelet components and the second wavelet component for the kth different resolution have a plurality of coefficients. The method further comprises, for each of the number of different resolutions, dividing coefficients for the first wavelet component into a first-subset of coefficients and a second-subset of coefficients based on a determined signal to noise ratio, comparing each coefficient in the first-subset of coefficient with a first variable threshold, and selectively changing a value of the coefficient in the first-subset of coefficients based on the comparison thereby generating a modified first subset of coefficients having changed coefficients and unchanged coefficients, comparing each coefficient in the second-subset of coefficients with a second variable threshold, and selectively changing a value of the coefficient in the second-subset of coefficients based on the comparison thereby generating a modified second subset of coefficients having changed coefficients and unchanged coefficients, and combining the modified first subset of coefficients with the second subset of coefficients.

The first variable threshold for each of the number of different resolutions are different, and the second variable threshold for each of the number of different resolutions are different.

The method further comprises transforming, using an inverse discrete wavelet transformation, at least the combined modified first subset of coefficients and the modified second subset of coefficients for each of the number of resolutions into a reversed in time denoised signal and reversing in time the reversed in time denoised signal to generate a denoised signal.

The signal may be an audio signal and/or a video signal. The signal may be streamed over a network. The network comprises at least one source server storing the signal, one or more relay nodes and a user terminal. A source server may comprises a processor configured to execute one or more of the methods of denoising a signal.

The signal may be acquired using a sensor. The sensor may be acceleration sensors, gyroscopes, seismometers, electrodes, light detectors and receivers. The result of the denoising, e.g., denoised signal, may be used as a control feedback for the acquisition of additional signals.

BRIEF DESCRIPTION OF FIGURES

FIG. 1b depicts a diagram of the denoising method depicted in FIG. 1a;

FIGS. 5a-6e depict a comparison between the denoising method depicted in FIGS. 1a and 1b and the other wavelet denoising methods for example 1;

FIGS. 7a-7f depict a comparison between the method depicted in FIGS. 1a and 1b and the other wavelet denoising methods for example 2;

FIG. 8 depicts a block diagram of a system for denoising signals in accordance with aspects of the disclosure;

FIG. 11b depicts a diagram of the denoising method depicted in FIG. 11a;

FIGS. 14a-18c depict a comparison of denoising methods for Sample 1 with 14 min of acquisition time;

FIGS. 19a-23c depict a comparison of denoising methods for Sample 2 with 8 min of acquisition time;

DETAILED DESCRIPTION

Figure 1A:
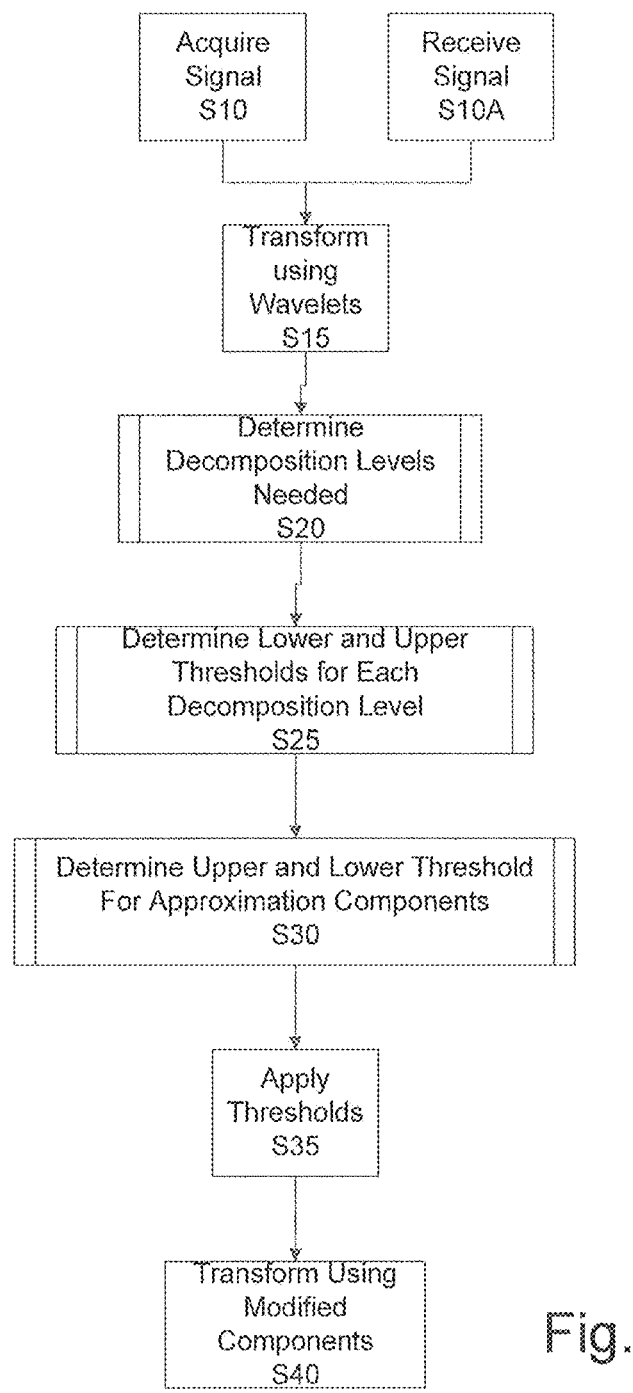
FIG. 1a depicts a flow chart for a method of denoising a signal in accordance with aspects of the disclosure.
Figure 1B:
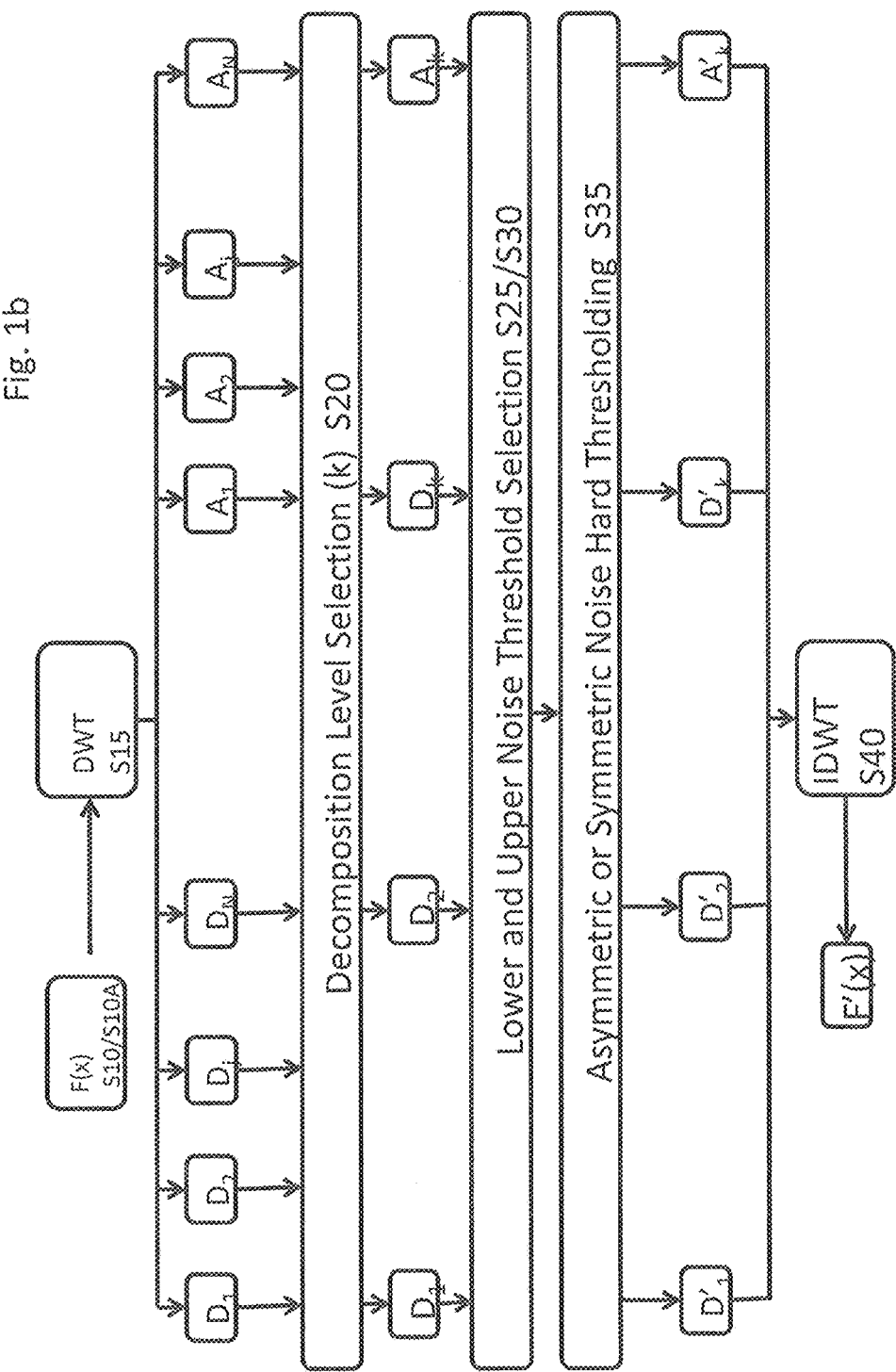

FIG. 1a depicts a flow chart for a method of denoising a signal in accordance with aspects of the disclosure. FIG. 1b depicts a diagram of the method including the detail and approximation components full scale, N and post selection decomposition level, k.

The method can be used to denoise many different types of signals for many different applications. For example, the signals can be acquired or generated by spectroscopy devices, such as continuous or pulsed Electron Spin Resonance spectroscopy, raman spectroscopy, nuclear magnetic resonance spectroscopy, mass spectroscopy, optical spectroscopy, infrared spectroscopy, laser spectroscopy, single molecule fluorescence spectroscopy and magnetic resonance imaging (spectroscopy). Additionally, the signals can be acquired or generated by microscopy devices such as Electron Spin Resonance Imaging and Microscopy, electron microscopy, including, but not limited to, cryo-electron microscopy (cyro-EM), multiphoton microscopy, confocal microscopy, and Magnetic Resonance Force Microscopy. Further, the signals can be acquired or generated by tomography devices, such as optical coherence tomography, positron emission tomography, and computed tomography. Additionally, the signals can be acquired or generated by other medical devices such as x-ray machine and ultrasounds. Moreover, the signals can be acquired by radar and sonar systems.

Yet additionally, the signals can be acquired by environmental sensors such as wind, gas, temperature, humidity, pressure, radiation levels, and seismometers.

Yet additionally, the signals can be transmitted and received via wired or wireless communication networks and can include audio and/or video.

The denoising methods described herein can be performed by separate standalone devices executing the method or part of a system such as audio/video streaming via a network, image video compression/decompression, power management and distribution, oil and gas exploration, where one or more devices within a system may execute any of the denoising methods described herein.

The signal may be 1-dimensional or multi-dimensional. In a case where the signal is multi-dimensional, the signal may be converted into a series of 1-dimensional signals and each 1-dimensional signal is denoised in accordance with the methods described herein. Once each of the 1-dimensional signals is denoised, the denoised signals may be aggregated to generate a denoised multi-dimensional signal.

At S10, the signal is acquired either via a sensor or retrieved from memory. In FIG. 1b, the acquired or received signal is identified as F(x). The sensor can be a component or components capable of have a response to a condition. For example, the sensor can be, but not limited to, acceleration sensors, gyroscopes, seismometers, electrodes, light detectors and receivers. The light detectors can be a photodiode, photoresistor, photovoltaic, thermopile and photoconductive detector. The sensor may also be an optical sensor.

Alternatively, the signal can be received via a network interface over a communication network S10A. The network interface may be configured for a wired or wireless network.

Once the signal is either acquired either via a sensor or retrieved from memory (S10) or received via the network (S10A), the signal is transformed using preset wavelet(s) into both detail (first set of components) and approximation (second set of components) (S15) by a processor. The detail components ($D_1$-$D_N$) and approximation components ($A_1$-$A_N$) are shown as the output of the DWT in FIG. 1b.

The transformation provides the original domain-frequency decomposition of the signal. This helps to separate noise and signal, as they typically do not possess the same time-frequency patterns. Wavelet transformation (WT) can either be continuous or discrete. For example, when the signal is a time-based signal, a continuous wavelet transform of a time-based signal S(t) is given as:

$$F(\tau, s) = \frac{1}{\sqrt{|s|}} \int_{-\infty}^{+\infty} S(t)\psi^*\left(\frac{t-\tau}{s}\right)dt \quad (1)$$

where τ (a time) and s (an inverse frequency) are respectively known as the translation and scale parameters, S(t) is the input signal, F (τ, s) is the continuous WT of the signal as a function of τ and s, and ψ*(t) is the complex conjugate of the wavelet function ψ*(t); for real wavelets, ψ*(t)=ψ(t). τ and s allow the study of time-frequency information of the input signal by varying the window width s and its translation τ.

A discrete wavelet transformation (DWT) of a time-based signal is given as follows:

$$D_j[n] = \sum_{m=0}^{p-1} S[t_m] 2^{j/2} \psi[2^j t_m - n] \tag{1A}$$

where now $s=2^{-j}$ and $\tau=n2^j$, with j and n integers, $t_m$ is the discretized time, $S[t_m]$ is the discretized input signal, $p=\text{length}(S[t_m])$, and $D_j[n]$ is the detail component of $S[t_m]$ at scale $2^j$, which is also known as the decomposition level j.

The transformation at S15 is for a maximum number of decomposition levels N (different resolutions). The number of decomposition levels allowed is N, where $N=[\log_2 p]$, i.e., $1 \leq j \leq N$, where N refers to the lowest frequency sub-band. p is defined above. The dyadic scale (i. e., $s=2^{-j}$) is selected so that the detail components $D_j[n]$ represent non-overlapping frequency bands. In another aspect of the disclosure, the detail components may have small overlapping frequency subbands. However, at decomposition levels 1 to j, only frequency sub-bands represented by them are wavelet-transformed, requiring that the remaining frequency band to reconstruct the original signal also be obtained.

For example, even at j=N, there is a low-frequency sub-band that is not covered because j is still constrained by the discrete finite signal of step length given by p. The remaining low frequency information contained in the wavelet transform of the signal is given by the Approximation component, which is defined as $$A_j[n] = \sum_{m=0}^{p-1} S[t_m] 2^{j/2} \phi[2^j t_m - n] \tag{2}$$

where $A_j[n]$ is the Approximation component at the $j^{th}$ decomposition level, and $\phi[t_m]$ is the discrete scaling function that allows the calculation of the low frequency part of the wavelet transform of the input signal. The wavelet function $\psi[2^j t_m - n]$ and the scaling function $\phi[2^j t_m - n]$ derived from it are orthogonal and of the same length.

There are many different wavelet families that can be preset. For example, the Coiflet, Daubechises and Symlet families are known wavelets. Wavelets that resemble the signal or its properties yield better signal and noise separation as well as sparsity. In an aspect of the disclosure, the wavelet family is chosen such that components, which are coherent, have a large magnitude in a few wavelet coefficients and coefficients occurring at the same location at the different detail components are achieved. By contrast, random noise will have many wavelet coefficients with small magnitudes that vary in location at the different detail components.

For example, a continuous wave electron spin resonance may be represented as a blend of function of Gaussian and Lorentzian and thus, a wavelet family suitable for such as spectra would be preset.

In an aspect of the disclosure, a wavelet family is selected to achieve:

$$\max(|w_j^{Noise} \geq 0|) < \min(|w_j^{Signal} \geq 0|) \tag{3}$$

$$\max(|w_j^{Noise} < 0|) < \min(|w_j^{Signal} < 0|) \tag{4}$$

$w_j$ are coefficients in the jth decomposition level.

At S20, the number of decomposition levels to denoise, e.g., threshold is determined by the processor. Smaller or greater maximum decomposition levels for denoising can result in under-denoising or signal distortion, respectively. A peak-to-sum ratio S is used to distinguish between noisy and noise-free detail components for a specific level.

Figure 2:
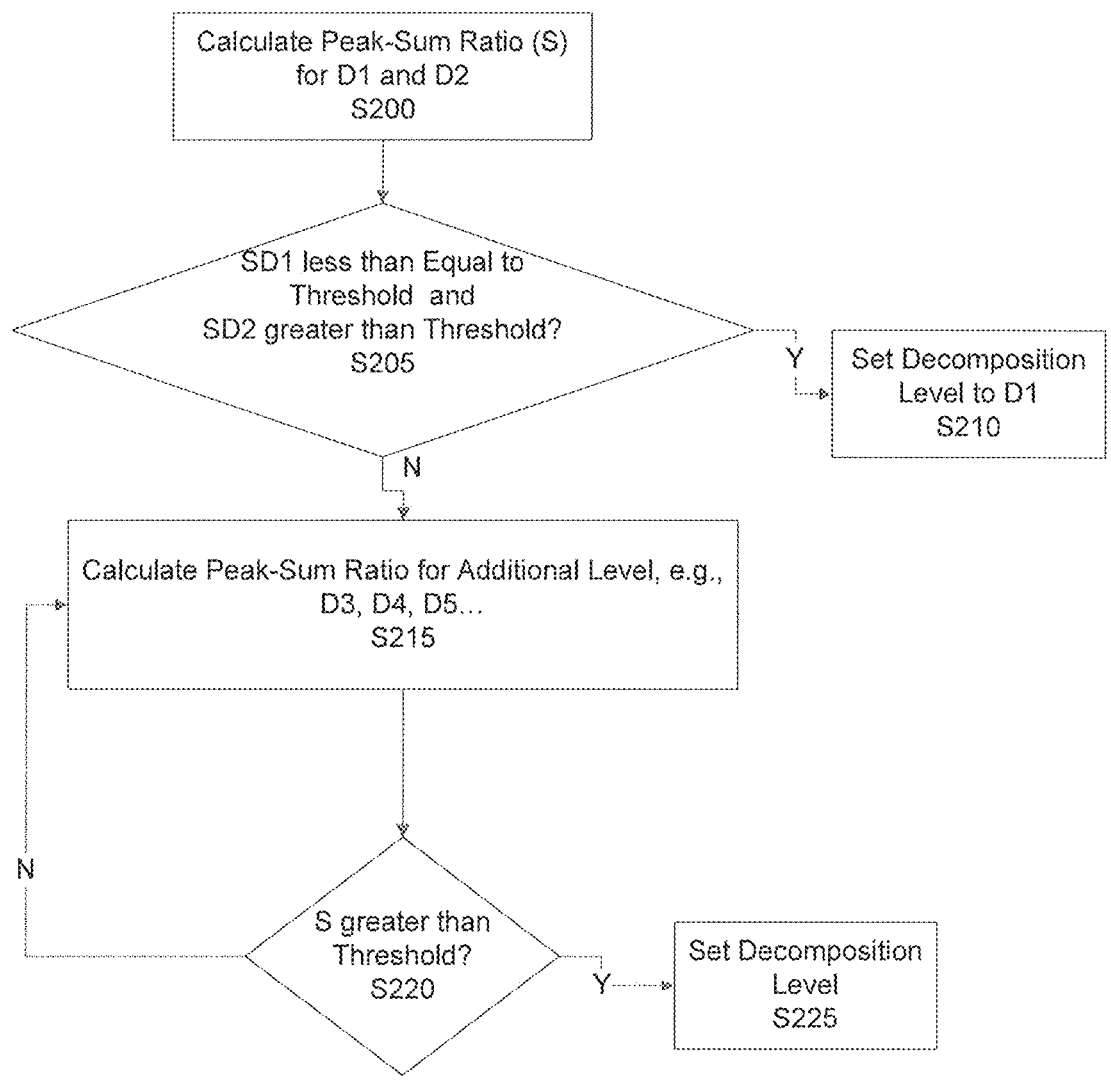
FIG. 2 depicts a flow chart for determining decomposition levels used in thresholding in accordance with aspects of the disclosure.

The method for determining the number decomposition levels is shown in FIG. 2.

The peak-to-sum ratio is defined as:

$$S_j = \frac{\max(|w_j|)}{\sum_{i=1}^{N_j} |w_{j,i}|} \tag{5}$$

$S_j$ reflects the sparsity of a detail component and allows the identification of noise presence in a detail component. Wj, i refers to the coefficients values for each of the components for a given decomposition level. Nj is the length or number of components for a given decomposition level.

A large $S_j$ indicates signal presence with only a few large coefficient values, where a small $S_j$ reveals noise presence with a large number of small coefficient value.

The $S_j$ can be categorized.

$S_j \leq 0.01$ indicates detail components that only contain noise coefficients;

$0.01 \leq S_j \leq 0.1$ indicates detail components that mainly contain noise with very few high magnitude signal coefficients;

$0.1 \leq S_j \leq T_r$ indicates detail components dominated by signal coefficients with noise coefficients having small magnitudes; and $S_j \geq T_r$ indicates detail components that only contain signal coefficients, e.g., noise is no longer distinguishable.

$T_r$ will be referred to herein as the decomposition threshold. The Sj for a specific decomposition level increases as the number of decomposition levels increases. The number of decomposition levels is selected such that the detail components only contain signal coefficients and where the noise is no longer distinguishable.

$$S_j < T_r, S_{j+1} > T_r, \text{ when } k=j, \text{ where } k \text{ is the maximum number of decomposition levels needed.} \tag{6}$$

$T_r$ is used to distinguish between detail components dominated by signal coefficients with noise coefficients having small magnitudes and detail components only containing signal coefficients. In an aspect of the disclosure $T_r$ is selected to be approximately 0.2.

As can be seen from equation 6, Sj must be calculated for at least two decomposition levels. At S200, the peak-to-sum ratio is calculated by a processor for the first two levels, e.g., D1 and D2 using equation 5. At S205, the processor determines if equation 6 is satisfied for D1 and D2, where D1 is j and D2 is j+1. If at S205, the processor determines that equation 6 is satisfied ("Y"), the processor sets the decomposition level needed for denoising to 1, e.g., k=1, otherwise, the calculation is repeated for an additional level at S215. At S220, the processor compares the calculated peak-to-sum ratio for the additional level with $T_r$. If the peak-to-sum ratio for the additional level is still less ("N"), S215 and S220 are repeated by the processor until the peak-to-sum ratio is greater than the $T_r$ for a given decomposition level as shown in equation 6. If the peak-to-sum ratio for a given deposition level is greater than $T_r$ (this become the j+1 level) ("Y" at S220), the processor sets the decomposition level k as one level less than the decomposition level for which the last peak-to sum ratio was calculated at S225. The set decomposition level k is stored in memory. The detail components in the set decomposition level k, i.e., $D_1$-$D_k$ are shown in FIG. 1b as being output of S20. $A_k$ is also output.

In another aspect of the disclosure, instead of the automated process for determining the decomposition levels k, as depicted in FIG. 2, a user may visually inspect the detail components and the corresponding approximation components. For example, $D_1$-$D_N$ and $A_1$-$A_N$, be displayed side-by-side on a display (see, e.g., FIG. 10). A user may select the detail components ($D_{1-k}$) to be denoised by including the decomposition levels until a level is reached in which noise is almost visible indistinguishable from the signal. The location and magnitude of signal and noise in the wavelet component are also useful, especially in identifying systematic noise. In all of the detail components, signals occur in the same locations with large magnitudes, whereas random noise appears inconsistently with small magnitudes and systematic noise usually occurs at a specific location with low magnitude. The amount of noise present in detail components reduce from decomposition level 1 to decomposition level N because noise usually contains more high frequencies than low frequencies. For very low SNR, an initial decomposition level(s), e g., 1 and 2 may contain just noise, whereas for high SNR, the last decomposition level may only contain signal.

Returning to FIG. 1a, at S25, the processor determines the denoise thresholds for each decomposition level used when thresholding the detailed components. For each level, there are two thresholds: a lower threshold and an upper threshold. The lower threshold is used for negative coefficients and the upper threshold is used for positive coefficients. The presence of signal and noise coefficients in the detail components may not result in a symmetric distribution of coefficients and a zero mean. For example, the coefficients of signal, systematic noise and other non-symmetric noise like Poisson noise, may create positive or negative bias in the detail components and thus result in the non-zero mean. Moreover, even random noise such as Gaussian noise is likely to have coefficient distribution bias.

Thus, in an aspect of the disclosure, the lower and upper thresholds do not need to be symmetric around zero. The two thresholds may be calculated using the following equations $$\lambda_{j,L} = \mu_j - \kappa_{j,L}\sigma_j \quad (7)$$

$$\lambda_{j,H} = \mu_j - \kappa_{j,H}\sigma_j \quad (8)$$

where $\lambda_{j,L}$ and $\lambda_{j,H}$ are the lower threshold and upper threshold, respectively, for the detail component at the $j^{th}$ Decomposition level, $\mu_j$ and $\sigma_j$ are the mean and standard deviation, respectively, of the detail component at the $j^{th}$ Decomposition level, and $\kappa_{j,L}$ and $\kappa_{j,H}$ are adjustable parameters to obtain optimal thresholds, respectively for the positive and negative coefficients to remove noise. Selecting the upper and lower thresholds are important and impact the performance of the denoising.

Figure 3:
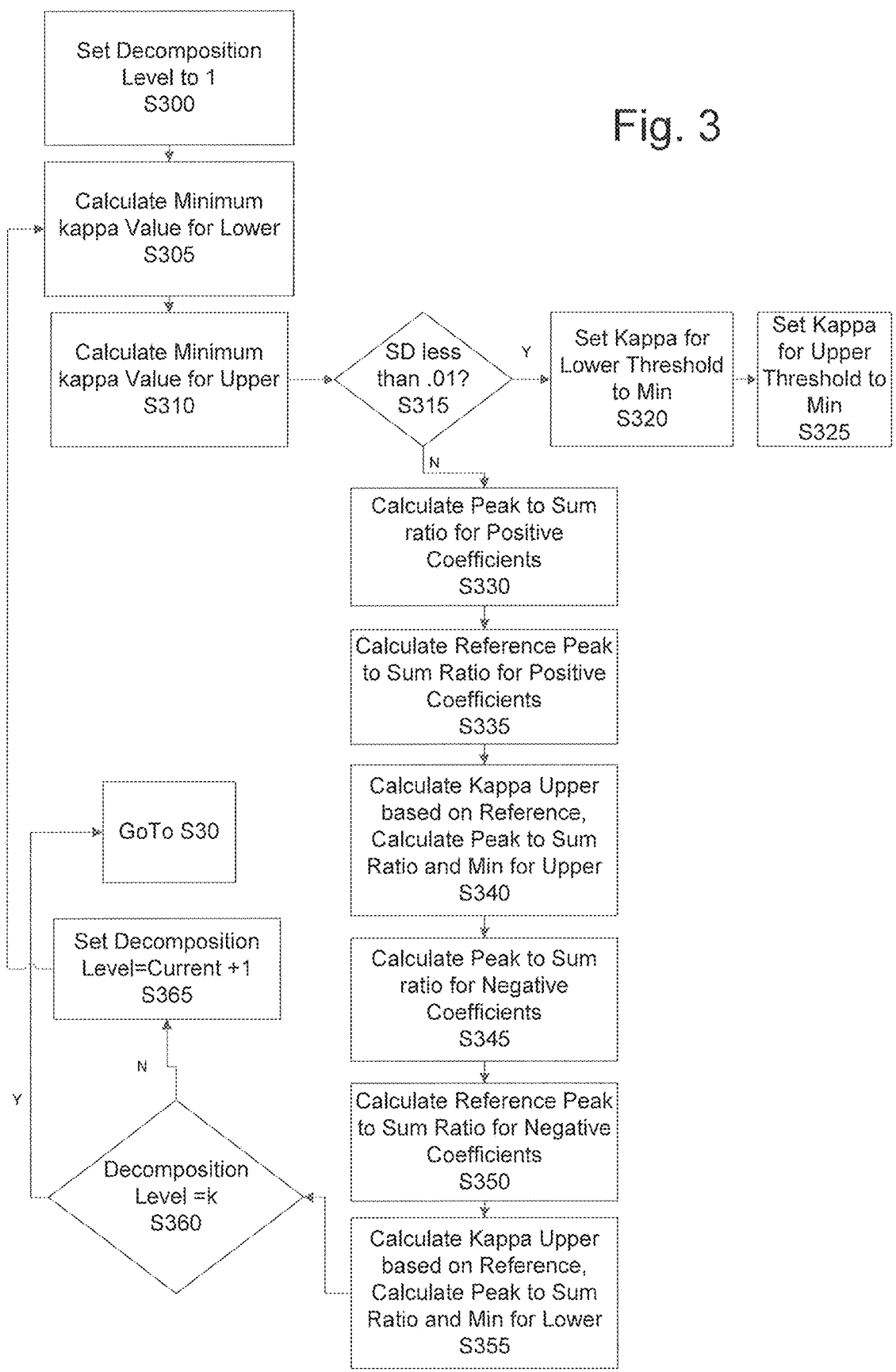
FIG. 3 depicts a flow chart for determining thresholds in accordance with aspects of the disclosure.

FIG. 3 depicts a flow chart for a method of determining the lower threshold and the upper threshold in accordance with aspects of the disclosure. As noted above, the thresholds are determined for each decomposition level, k determined to be used for thresholding, e.g., 1-k. In an aspect of the disclosure, the thresholds may be determined, one level at a time, starting with decomposition level 1. Thus, at S300, the processor sets the level for analysis, e.g., level 1. The processor may use a counter to count the decomposition levels. The thresholds are stored in memory for each decomposition level used for thresholding. The setting of the level may also include setting a memory location to store the associated thresholds. Minimum $\kappa_{j,Lmin}$ and $\kappa_{j,Hmin}$ are respectively determined by the processor at S305 and S310. $\kappa_{j,Lmin}$ and $\kappa_{j,Hmin}$ are the minimum values that cover all of the coefficients in a given decomposition level.

$\kappa_{j,Lmin}$ is determined by the following equations:

$$k_{j,L_{min}} = \frac{\mu_j - \max(|w_j < 0|)}{\sigma_j} \quad (9)$$

$\kappa_{L,Hmin}$ is determined by the following equations:

$$k_{j,H_{min}} = \frac{\max(|w_j > 0|) - \mu_j}{\sigma_j} \quad (10)$$

As previously described, when a peak-to-sum value S for a given decomposition level is less than 0.01, the component only contain noise coefficients and thus all coefficient of the detail component can be assigned to zero. Therefore, at S315, the processor compares the previously calculated peak-to-sum value with 0.01. If the peak-to-sum value S≤0.01, then the processor sets $\kappa_{j,L} = \kappa_{j,Lmin}$ at S320 and sets $\kappa_{j,H} = \kappa_{j,Hmin}$ S325. The $\lambda_{j,L}$ in turn would be calculated using equation 7 and $\lambda_{j,H}$ would be calculated using equation 8.

If the peak-to-sum value is greater than 0.01, both signal and noise coefficients are present. Accordingly, the minimum κ values for both the lower and the upper threshold must be scales given that the magnitude of the noise coefficients are less than that of the signal coefficients, e.g., $\kappa_{j,L} < \kappa_{j,Lmin}$ and $\kappa_{j,H} < \kappa_{j,Hmin}$.

In an aspect of the disclosure, the processor separately calculates the peak-to-sum ratios for both the positive coefficients (S330) and the negative coefficients (S345).

The peak-to-sum for the negative coefficients $S_j$, L is determined using the following equation $$S_{j,L} = \frac{\max(|w_j < 0|)}{\sum_{i=1}^{N_j} |w_{j,i} < 0|} \quad (11)$$

The denominator in equation 11 adds the absolute value of all of the negative coefficients in a given decomposition level.

The peak-to-sum for the positive coefficients $S_j$, H is determined using the following equation $$S_{j,H} = \frac{\max(|w_j \geq 0|)}{\sum_{i=1}^{N_j} |w_{j,i} \geq 0|} \quad (12)$$

The denominator in equation 12 adds the absolute value of all of the positive coefficients in a given decomposition level.

The processor also separately calculates reference peak-to-sum ratios for both the positive coefficients (S335) and the negative coefficients (S350). The reference peak-to-sum ratio uses peak-to-sum ratios from both a decomposition level one greater than the determined decomposition level, k, (i.e., k+1) as well as the determined decomposition level, k. For example, if k=5, the reference peak-to-sum ratio is determined from peak-to-sum values for the $5^{th}$ and $6^{th}$ decomposition levels.

The upper reference peak-to-sum ratio $S_{r,H}$ is determined by the processor using the following equation at S335:

$$S_{r,H} = (S_{k,H} + S_{k+1,H})/2 \tag{13}$$

The lower reference peak-to-sum ratio $S_{r,L}$ is determined by the processor using the following equation at S350:

$$S_{r,L} = (S_{k,L} + S_{k+1,L})/2 \tag{14}$$

At S340 and S355, the processor separately calculates $\kappa_{j,L}$ and $\kappa_{j,H}$ using the following equations:

$$k_{j,L} = \left(\frac{S_{r,L} - S_{j,L}}{S_{r,L}}\right) k_{j,L_{min}} \tag{15}$$

$$k_{j,H} = \left(\frac{S_{r,H} - S_{j,H}}{S_{r,H}}\right) k_{j,H_{min}} \tag{16}$$

Once $\kappa_{j,L}$ and $\kappa_{j,H}$ are determined, the processor can use equations 7 and 8 to calculate $\lambda_{j,L}$ and $\lambda_{j,H}$ for a given decomposition level. $\lambda_{j,L}$ and $\lambda_{j,H}$ are then stored in memory.

In an aspect of the disclosure, $\kappa_{j,L}$ and $\kappa_{j,H}$ may also be adjusted to a value different than calculated under certain conditions, if needed. For example, even when $S_j \geq 0.01$, a detail component(s) may have only noise coefficients due to one or more large random noise spikes, and $\kappa_{j,L_{min}}$ and $\kappa_{j,H_{min}}$ may be used instead of the calculated values from equations 15 and 16. Similarly, in a noise-dominated detail component(s) either positive or negative coefficients are all noise and $K_{j,L_{min}}$ and $\kappa_{j,H_{min}}$ may be used instead of the calculated values from equations 15 and 16.

Additionally, when small signal and large noise coefficient values are comparable, $\kappa_{j,L}$ and $\kappa_{j,H}$ may be slightly increased or decreased to separate the signal and noise coefficients.

S305-S355 are repeated for each decomposition level used for denoising, i.e., 1-k. Thus, at S300 the processor determines if the thresholds have been determined for all of the k decomposition levels. In other words, the processor determines if the decomposition level whose thresholds were calculated is k (the final decomposition level used). If "N", then the processor increments the decomposition level for processing by 1 (S365) and returns to S305 to start the process for the next decomposition level.

If "Y" at S360, the processor go to to S30 to determine the upper threshold and lower threshold for the approximation component for decomposition level k.

The determination of the upper and lower threshold for the approximation component is the same as described above S305-S355 and will not be described again.

Once all of the thresholds (the lower threshold and the upper threshold for each decomposition level and the upper threshold and lower threshold for the approximation) are determined and stored, the processor executes a thresholding of the components at S35. In an aspect of the disclosure, a hard thresholding is used. Unlike certain conventional techniques that use soft thresholding, hard thresholding ensure that the signal wavelet coefficients are not distorted by the thresholds, especially when signal and noise coefficients are disjoint and not superimposed. Using the thresholds determined above, noise present at a signal location is separated in the initial decomposition levels and removed. For the detail components, the thresholding is done at each of the decomposition levels used to denoise, e.g., 1-k and for the approximation component, the thresholding is done at the decomposition level k only (unlike conventional techniques which do not threshold the approximation components). However, certain signals may contain substantial low frequency noise (especially at low SNR) that impedes analysis. Thus, the approximation component(s) may also contain low frequency noise and should be denoised.

Depending on the signal properties and the choice of wavelets, the kth approximation component may represent low frequency noise and signal coefficients in a relatively sparse manner allowing for the noise to be removed. The signal coefficients would have larger values than the noise coefficients.

The processor uses the following equation for thresholding both detail and approximation coefficients:

$$\tilde{w}_{j,i} = \begin{cases} 0, & \text{for } \lambda_{j,L} \leq w_{j,i} \leq \lambda_{j,H} \\ w_{j,i} & \text{otherwise} \end{cases} \tag{17}$$

$w_{j,i}$ is the ith detail coefficient at the jth decomposition level, $\tilde{w}_{j,i}$ is the thresholded wavelet coefficients. FIG. 1b shows the output of S35 being the denoised detailed components $D'_1$-$D'_k$ and denoised approximation component $A'_k$.

In another aspect of the disclosure, prior to S40, the denoised detail components $D'_1$-$D'_k$ and denoised approximation component $A'_k$ may be displayed on a display side-by-side with the corresponding $D_1$-$D_k$ and approximation component $A_k$. A user may visually compare the denoised components with the corresponding noised components and adjust $\kappa_{j,L}$ and $\kappa_{j,H}$ based on the comparison.

At S40, the processor performs an inverse discrete transformation to recover a denoised signal (shown in FIG. 1b as F'(x) using the denoised (modified) detail components from each of the decomposition levels and the denoised (modified) approximation component at decomposition level k.

Testing and Comparison to Other Methods

Example 1

The above method was tested for signals generated from a cw-ESR system. The ESR was performed at 20° C. using a spectrometer (BRUKER ELEXYS-II E500) at a microwave frequency of 9.4 GHz (X-band), which is standard (corresponding to a DC magnetic field of 0.34 Telsa).

The frequency was held constant and the magnetic field was swept through resonance to obtain and ESR spectrum. The sample consisted of 4 μL of a 100 μM aqueous solution of spin-probe molecule Tempol (4-Hydroxy-2,2,6,6-Tetramethylpiperidine 1-oxly). The sample was placed in a glass capillary of 0.8 mm ID, which was subsequently introduced into the microwave cavity situated between the pole caps of the dc magnet. The magnetic field was then swept over a range of 60 G corresponding to the resonant spectral range for a period of 2 minutes and a 82 ms time constant was used.

The spectral data consisted of 4096 points along the magnetic-field sweep.

In addition, small coils place at the sides of the resonator provided a small magnetic field modulation of +−0.02G at a frequency of 100 kHz. The 100 kHz modulated ESR signal was detected with a lock-in detector at this frequency, providing a first derivative of the absorption signal. A low power 0.2 mW microwave radiation was used to avoid saturation the ESR.

Multiple scan were performed with a delay of 4 s between scans. The results of the scans were averaged. By averaging different number of scans, different SNRs were obtained.

As a reference signal, the signal averaged over 500 scans was used for a comparison with the denoised signals.

The SNR was calculated using the following equation:

$$SNR = \frac{Signal_{Peak}}{Noise_{RMS}} \quad (18)$$

or in decibels (dB)

$$SNR = \frac{20\log 10(SignalPeak\text{-to-Peak})}{Noise_{rms}} \quad (19)$$

where rms is the root mean square.

SNR measures both distorting (i.e., structural) and non-distorting (i.e., nonstructural) noise in the signal, but it cannot differentiate between them.

Thus, a structure similarity index measure (SSIM) was used as another objective measure. The SSIM enables the estimation of the structural similarity or fidelity of the noisy and of the denoised signals at 4 and 16 scans (shown herein) with respect to the reference 500 scan signal. The SSIM is calculated as:

$$SSIM(X, Y) = \frac{(2\mu_X\mu_Y + c_1)(2\sigma_{XY} + c_2)}{(\mu_X^2 + \mu_Y^2 + c_1)(\sigma_X^2 + \sigma_Y^2 + c_2)} \quad (20)$$

where X is either the noisy or denoised signal; Y is the reference signal, $\mu_x$ and $\mu_y$ are the mean values of X and Y, respectively, $\sigma_x$ and $\sigma_y$ are the standard deviation values of X and Y, respectively, $\sigma_{XY}$ is the covariance of X and Y and $c_1$ and $c_2$ are small positive constants used for stabilizing each term.

The SSIM value ranges between −1 and 1 and is 1 when X is identified to Y. The more that X is structurally reassembly Y, the SSIM will be closed to 1.

As the wavelet, the coiflet 3 was used because it best resembles the spectra. An ESR spectrum is frequently composed of Lorentzian and Gaussian functions, or mixtures of both. A $T_r$=0.20 was used.

The method described above was compared with conventional denoising methods include SUREShrink and Minimax (using both hard and soft thresholding) as well as other wavelet denoising methods.

The decomposition level k that yields maximum SNR compared to other decomposition levels was selected as the decomposition level k for the conventional denoising methods.

In the above table "Hard" refers to hard thresholding; "Soft" refers to soft thresholding; DL is the decomposition level used: dB is the SNR in decibels.

The method referred to as Zhao is described in R.-M. Zhao and H.-M. Cui, "Improved threshold denoising method based on wavelet transform," in *Proc. 7th Int. Conf. Modelling, Identificat. Control (ICMIC)*, 2015, pp. 1-4, which is incorporated by reference. The method referred to as Poornachandra is described in S. Poornachandra, N. Kumaravel, T. K. Saravanan, and R. Somaskandan, "Wave-Shrink using modified hyper-shrinkage function," in *Proc. 27th Annu. Int. Conf. Eng. Med. Biol. Soc. (IEEE-EMBS)*, January 2005, pp. 30-32, which is incorporated by reference. The method referred to as Zhang is described in D. Zhang and P. Bao, "Denoising by spatial correlation thresholding", *IEEE Trans. Circuits Syst. Video Technol.*, vol. 13, no. 6, pp. 535-538, June 2003, which is incorporated by reference. The method referred to as Lin is described in Y. Lin and J. Cai, "A new threshold function for signal denoising based on wavelet transform," in *Proc. IEEE Int. Conf. Meas. Technol. Mechatronics Autom.*, March 2010, pp. 200-203, which is incorporated by reference.

As can be clearly seen from Table 1, the above described method achieves a denoised signal having a significantly better SNR. The SNR (in db) doubles from the noisy spectrum and is more than 20 db greater than the conventional wavelet denoising methods. Moreover, the above described method achieves a denoised signal having a better structural similarity with the reference.

TABLE 2

Computational Time: Comparison of the method described above ("New Method") with conventional wavelet denoising methods

| | Computation Time (seconds) | |
|---|---|---|
| Method | 16 scans | 4 scans |
| Minimax-Hard | 0.0804 | 0.0834 |
| Minimax-Soft | 0.0807 | 0.0788 |
| SUREShrink-Hard | 0.0853 | 0.0878 |
| SUREShrink-Soft | 0.0873 | 0.0866 |
| Zhao | 0.0864 | 0.0864 |
| Poornachandra | 0.0857 | 0.0849 |
| Zhang | 0.0858 | 0.0855 |
| Lin | 0.0867 | 0.0852 |
| New Method | 0.0131 | 0.0140 |

Table 2 shows the actual computation times and was calculated in MATLAB on a 64-bit operating system with 16

TABLE 1

Comparison of the method described above ("New Method") with conventional wavelet denoising methods are 16 and 4 scans.

| | 16 scans | | | | 4 scans | | | |
|---|---|---|---|---|---|---|---|---|
| Method | SNR (dB) | SNR | SSIM | DL | SNR (dB) | SNR | SSIM | DL |
| Noisy | 35 | 57 | 0.9903 | — | 30 | 32 | 0.9684 | — |
| Minimax-Hard | 43 | 146 | 0.9959 | 7 | 38 | 81 | 0.9880 | 7 |
| Minimax-Soft | 46 | 201 | 0.9954 | 7 | 41 | 114 | 0.9890 | 12 |
| SUREShrink-Hard | 38 | 82 | 0.9938 | 9 | 32 | 41 | 0.9779 | 9 |
| SUREShrink-Soft | 44 | 157 | 0.9966 | 7 | 37 | 77 | 0.9905 | 12 |
| Zhoa | 46 | 209 | 0.9821 | 6 | 38 | 80 | 0.9790 | 6 |
| Poornachandra | 44 | 167 | 0.9825 | 6 | 37 | 73 | 0.9803 | 6 |
| Zhang | 46 | 209 | 0.9821 | 6 | 38 | 80 | 0.9778 | 6 |
| Lin | 44 | 167 | 0.9825 | 6 | 38 | 79 | 0.9800 | 6 |
| New Method | 73 | 4438 | 0.9969 | 6 | 64 | 1567 | 0.9957 | 6 |

GB RAM and a 3.30 GHz processor. The computation time was measured 5000 times and then averaged. As can be seen from Table 2, the above described method is 6 times faster than the conventional denousing methods.

Figures 4A, 4B, 4C, 4D:
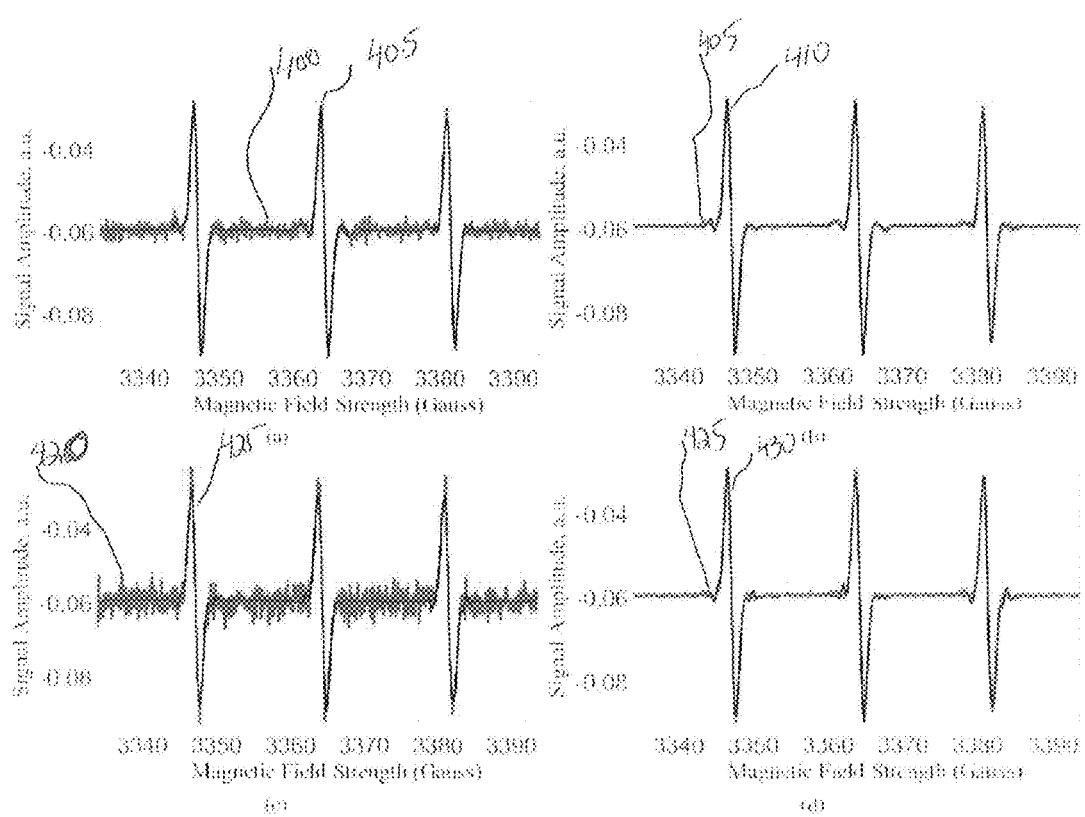
FIGS. 4a-4d depict test results for the denoising method depicted in FIGS. 1a and 1b; 4a showing a comparison of a denoised signal in accordance with aspects of the disclosure and a noised signal (from 16 scans); 4b showing a comparison of a denoised signal (from 16 scan) in accordance with aspects of the disclosure and a reference signal; 4c showing a comparison of a denoised signal in accordance with aspects of the disclosure and a noised signal (from 4 scans); 4d showing a comparison of a denoised signal (from 4 scans) in accordance with aspects of the disclosure and a reference signal.

FIG. 4a depicts a comparison of a denoised signal 405 based on the above-described method with a noisy signal 400 (from 16 scans). FIG. 4b depicts a comparison of the denoised signal 405 with a reference signal 410 (obtained from 500 scans). FIG. 4c depicts a comparison of a denoised signal 425 based on the above-described method with a noisy signal 420 (from 4 scans). The noisy signal 420 has more noise than the noisy signal 400. FIG. 4d depicts a comparison of the denoised signal 425 with a reference signal 410 (same reference signal obtained from 500 scans). As can be seen from FIGS. 4a and 4c, the method successfully recovers the signal peaks and removes the baseline noise (from the superimposed signals). Also, the above method is able to distinguish the small satellite peaks (adjacent the large peaks) that were submerged and concealed in the noise (which is better seen in FIGS. 4b and 4d).

FIGS. 5a-6e show a comparison between the above method and the conventional wavelet denoising methods. The noisy signal is identified as "400" in FIGS. 5a-6e. The reference signal is identified as "410" in FIGS. 5a-6e. The above described method (identified as new method) is shown in FIGS. 5a and 6a for ease of comparison (denoised signal is identified as "405" in FIGS. 5a and 6a). The left side of each Fig. is a comparison of the denoised signal for the respective method and the noisy signal (the denoised signal in each respective conventional method is identified as $405_{b-e}$ in FIGS. 5a-5e and $605_{b-e}$ in FIGS. 6a-6e) and the right side of each row is a comparison of the denoised signal for the respective method with the reference signal.

Example 2

An ESR spectrum was obtained under different conditions from above to provide a different and more complex spectrum for denoising. It was obtained on a home-built (ACERT) 95 GHz ESR spectrometer with a dc magnetic field of 3.3 Tesla at 25° C. The sample used contained ca. 5 µL of phospholipid vesicles doped with 0.5% of a lipid spin label: 16-PC (1-acyl-2-[16-(4,4-dimethyloxazolidine-N-oxyl)stearoyl]-sn glycero-3-phosphocholine) in the fluid phase that had been suspended in water. The sample was placed in a disc-like sample holder utilized for millimeter-wave ESR methodology.

The acquisition parameters were: sweep width of 250 G, sweep time of 2 min with a time constant of 100 ms. The millimeter-wave power was 16 mW and the spectrum consists of 512 points. The field modulation parameters were: 6 G modulation amplitude and 100 kHz modulation frequency.

The signal used for denoising was an average of 100 scans. The time between scans was 3 s.

TABLE 3

Comparison of Signal to Noise Ratio (SNR) of the method described above ("New Method") with conventional wavelet denoising methods

| Method | SNR (dB) | SNR | DL |
| --- | --- | --- | --- |
| Noisy | 33 | 49 | — |
| Minimax-Hard | 38 | 81 | 10 |
| Minimax-Soft | 43 | 149 | 6 |
| SUREshrink-Hard | 37 | 76 | 7 |

TABLE 3-continued

Comparison of Signal to Noise Ratio (SNR) of the method described above ("New Method") with conventional wavelet denoising methods

| Method | SNR (dB) | SNR | DL |
| --- | --- | --- | --- |
| SUREShrink-Soft | 41 | 115 | 9 |
| Zhang | 44 | 167 | 6 |
| New Method | 165 | $191 \times 10^6$ | 4 |

In the above table "Hard" refers to hard thresholding; "Soft" refers to soft thresholding; DL is the decomposition level used: dB is the SNR in decibels. As can be clearly seen from Table 3, the above described method achieves a denoised signal having a significantly better SNR. The SNR (in db) of the denoised signal in accordance with the above described method is more than 120 db greater than the conventional wavelet denoising methods.

FIGS. 7a-7f show a comparison between the above method and the other wavelet denoising methods. The above described method (identified as New Method) is shown in FIG. 7a. The noisy signal is identified as "700" in FIGS. 7a-7f. The denoised signal is respectively identified as $705_{a-f}$. The denoised signal that resulted from the above described method is $705_a$.

Each figure is a comparison of the denoised signal according to the respective method and noised signal. As can be seen in FIGS. 7b-7f, the "denoised signals" still contain noisy artifacts which is reflected in many peaks/valleys, whereas the denoised signal in FIG. 7a is smooth.

System

FIG. 8 depicts a block diagram of a system 890 for denoising signals in accordance with aspects of the disclosure. The system 890 includes a source server 800, a plurality of relays 825 and a user terminal 850. The signals may be video or audio and may be streamed over a communication network, for example, using an Internet connection. The Source Server 800 comprises a processor 805, memory 810 and a network interface 815. The memory 810 may be, but not limited to, RAM, ROM and persistent storage. The memory is any piece of hardware that is capable of storing information, such as, for example without limitation, data, programs, instructions, program code, and/or other suitable information, either on a temporary basis and/or a permanent basis.

The processor 805 may be a CPU. The CPU may be configured to execute one or more programs stored in a computer readable storage device such as the memory 810. For example, the CPU may be configured to execute a program causing the CPU to perform the above described denoising method. The memory 810 further stores video and audio files or data. The video file may include a movie for streaming. The audio file may include a song for streaming. The memory 810 may stored the decomposition levels used for denoising, upper and lower thresholds, the denoised signal, the detailed components and approximation components, denoised detailed components and denoising approximation components. In an aspect of the disclosure, the memory 810 may also include target SNR.

The processor 805 may perform the above-described denoising method before compression or encoding the video for transmission. In another aspect of the disclosure, the processor 805 may perform the above-described denoising method during compression or encoding the video for transmission.

In another aspect of the disclosure, the processor 805 may calculate a signal to noise ratio for the denoised signal (video or audio) prior to transmission. Based on the calculated SNR for the denoising signal, the processor 805 may control the bit rate for the transmitted signal. Advantageously, by denoising the signal in accordance with the above described method, prior to the transmission of the signal, a higher bit rate may be achieved which will result in a reduction of bandwidth needed to transmit the signal (video or audio).

The network interface 815 may be a wired or wireless interface capable of transmitting and receiving.

The relays 825 are electronic communications equipment were are placed between the source server 800 and a user terminal 850 such that the signals may be transmitted between the source server 800 and the user terminal 850. The relay 825 may be a cell tower (base station), a mobile terminal such as a smartphone, a tablet, a laptop, and etc., a router, a switch, and a repeater. Although not shown in FIG. 8, each relay includes a network interface for transmitting and receiving signals.

The user terminal 850 may include a network interface 815 (which may be the same as the network interface in the source server 800), a display 855, speaker(s) 860, memory 865 and a processor 870. The processor 870 also may be a CPU. The CPU may be configured to decode and decompress a video and cause the display 855 to display the same. The CPU may also be configured to cause the speakers to play the audio associate with the video as well as audio from a separate audio signal.

Each time a signal is relayed by the relay 825 (multiple hops) noise may be added to the signal. For example, if the network has a portion thereof that is wired, noise may be caused by the connection cables or electrical components of the relay itself.

Therefore, in an aspect of the disclosure, the relay 825 further includes a processor configured to execute the above described denoising method on the signal prior to relaying to either a subsequent relay or the user terminal 850.

In another aspect of the disclosure, processor 870 in the user terminal may execute the denoising method on the signal received before or during the decoding and decompression.

Figure 9:
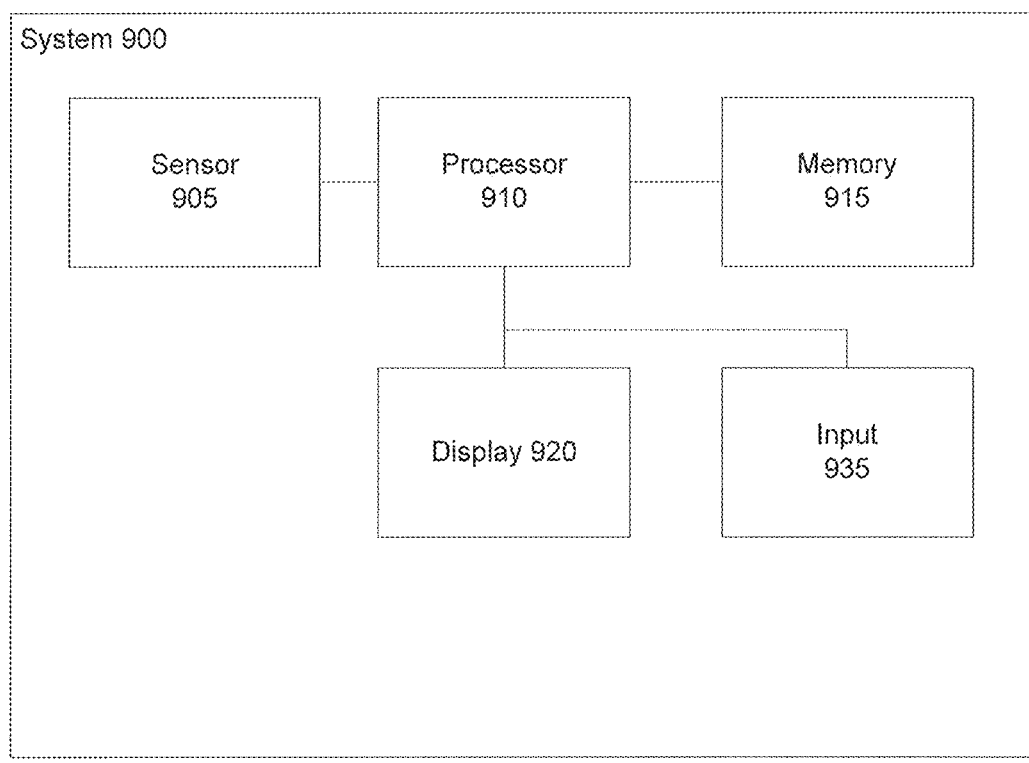
FIG. 9 depicts a block diagram of another system for denoising signals in accordance with aspects of the disclosure.

FIG. 9 depicts a block diagram of another system 900 for denoising signals in accordance with aspects of the disclosure.

System 900 include a sensor 905 (acquisition sensor), a processor 910, memory 915, a display 920 and an input 935. As described above, the sensor 905 may be any component or components capable of have a response to a condition, such as, but not limited to, acceleration sensors, gyroscopes, seismometers, electrodes, light detectors and receivers.

In an aspect of the disclosure, the sensor 905 is connected to the processor 910. For example, the sensor 905 may be indirectly connected to the processor 910 via an optical cable running between the sensor 905 and a communication port. In another aspect of the disclosure, the sensor 905 may be connected to the processor 910 via a circuit board trace. The processor 910 may be a CPU.

In an aspect of the disclosure, the processor 910 may control the acquisition of a signal and execute the above described denoising method. The processor 910 may cause the display 920 to display a noisy signal, the denoised signal, the detailed components and approximation components, denoised detailed components and denoising approximation components.

The input 935 may be a keyboard, a mouse, or a touch panel.

The memory 915 may be, but not limited to, RAM, ROM and persistent storage. The memory is any piece of hardware that is capable of storing information, such as, for example without limitation, data, programs, instructions, program code, and/or other suitable information, either on a temporary basis and/or a permanent basis. The memory 915 may store the raw data acquired by the sensor 905, e.g., noisy signal. The memory 915 may include programs for execution by the processor such as the CPU including a program for causing the CPU to execute the above described denoising method(s). The memory may stored the decomposition levels used for denoising, upper and lower thresholds, the denoised signal, the detailed components and approximation components, denoised detailed components and denoising approximation components. In an aspect of the disclosure, the memory 915 may also include target SNR.

In an aspect of the disclosure, the processor 910 may execute the denoising method for each acquisition (or detection) by the sensor 905. In another aspect of the disclosure, the processor 910 may average a preset number acquisition (or detections) by the sensor 905 and wait until the preset number of acquisitions has been reached prior to execution of the denoising method.

In another aspect of the disclosure, the processor 910, after denoising the signal, may calculate a signal to noise ratio (SNR) for the denoised signal. The processor 910 may compare the calculated SNR to a target SNR stored in memory 915. If the calculated SNR has reached or exceeded the target SNR, the processor 910 may cause the sensor 910 to stop acquiring a signal or cause the sensor 910 to acquire a signal representing a different data point. Advantageously, since the system 900 provides a high SNR denoised signal, the number of acquisition needed to provide the target SNR signal is minimize. Typically, averaging of multiple acquisition increases the SNR of the averaged signal. Therefore, since the system can achieve the high SNR using fewer acquisitions, time for acquiring the data (for each data point) is reduced (as well as a cost savings).

In an aspect of the disclosure, the system 900 may be a part of a MRI system or a CT system. The sensor 905 is located in a separate room from the processor 910 (and the other components in FIG. 9). The signal may represent one or more scans of data. The memory 915 will also store a program for controlling the MRI system or CT system. For example, the processor 910 causes the MRI or CT to execute a scan and the results of which are detected by the sensor 905. Between each scan, the processor 910 may execute the denoising method on a single scan signal or an average of multiple scan signals. The result is a denoised signal either for a single scan or the average of multiple scans.

Prior to causing the MRI or CT to execute another scan in the same position, the processor 910 may calculate an SNR for the denoised signal and compare the same with the target SNR. When the target SNR is reached, there is no need for executing another scan at the same position. Therefore, the processor 910 may control the MRI or CT to move the scan to a different position (or end).

In another aspect of the disclosure, as part of the denoising, the processor 910 may cause the display 920 to display the denoised detail components and the noised detail components side-by-side for comparison. A user, using the input 935, may input a change in the scaling parameters $\kappa_{j,L}$ and $\kappa_{j,H}$ for the upper and lower thresholds, for one or more decomposition levels. Subsequently, the processor 910 will re-execute the thresholding of the detail components and/or the kth approximation component using the new thresholds (S35) and subsequently re-executing the inverse transformation (S40).

Figure 10:
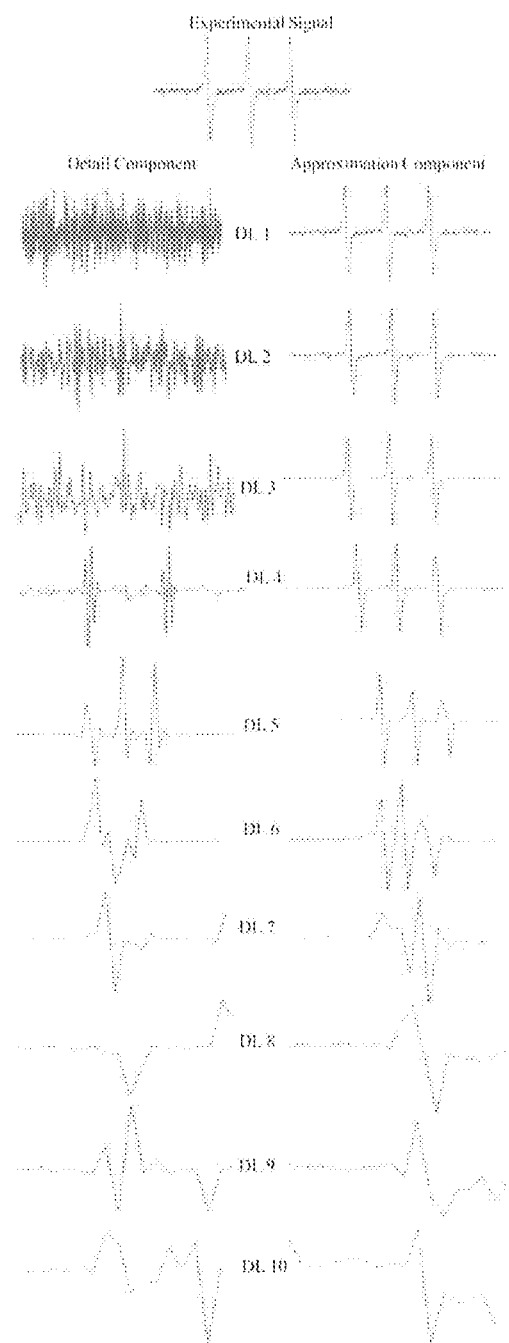
FIG. 10 depicts an example of detail and approximation components of a signal for a full scale decomposition.

In another aspect of the disclosure, as part of the denoising, the processor 910 may cause the display 920 to display the full scale detail and approximation components for a selection of the decomposition levels to denoise. An example of which is shown in FIG. 10. The user, using the input 935 may input a decomposition level and the processor 910 will execute the thresholding for only the selected decomposition levels.

Figure 11A:
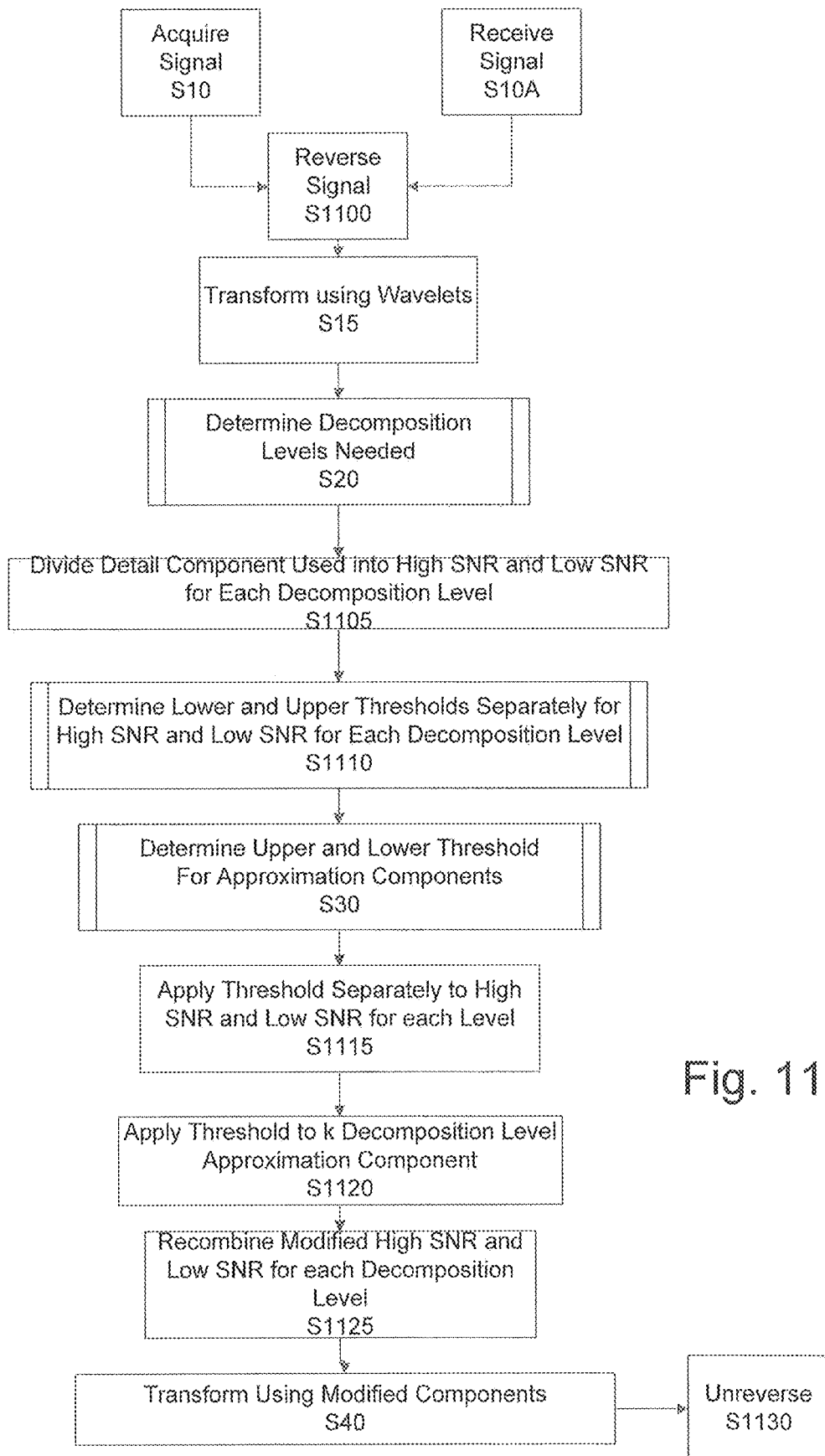
FIG. 11a depicts a flow chart of another method of denoising signals in accordance with aspects of the disclosure.
Figure 11B:
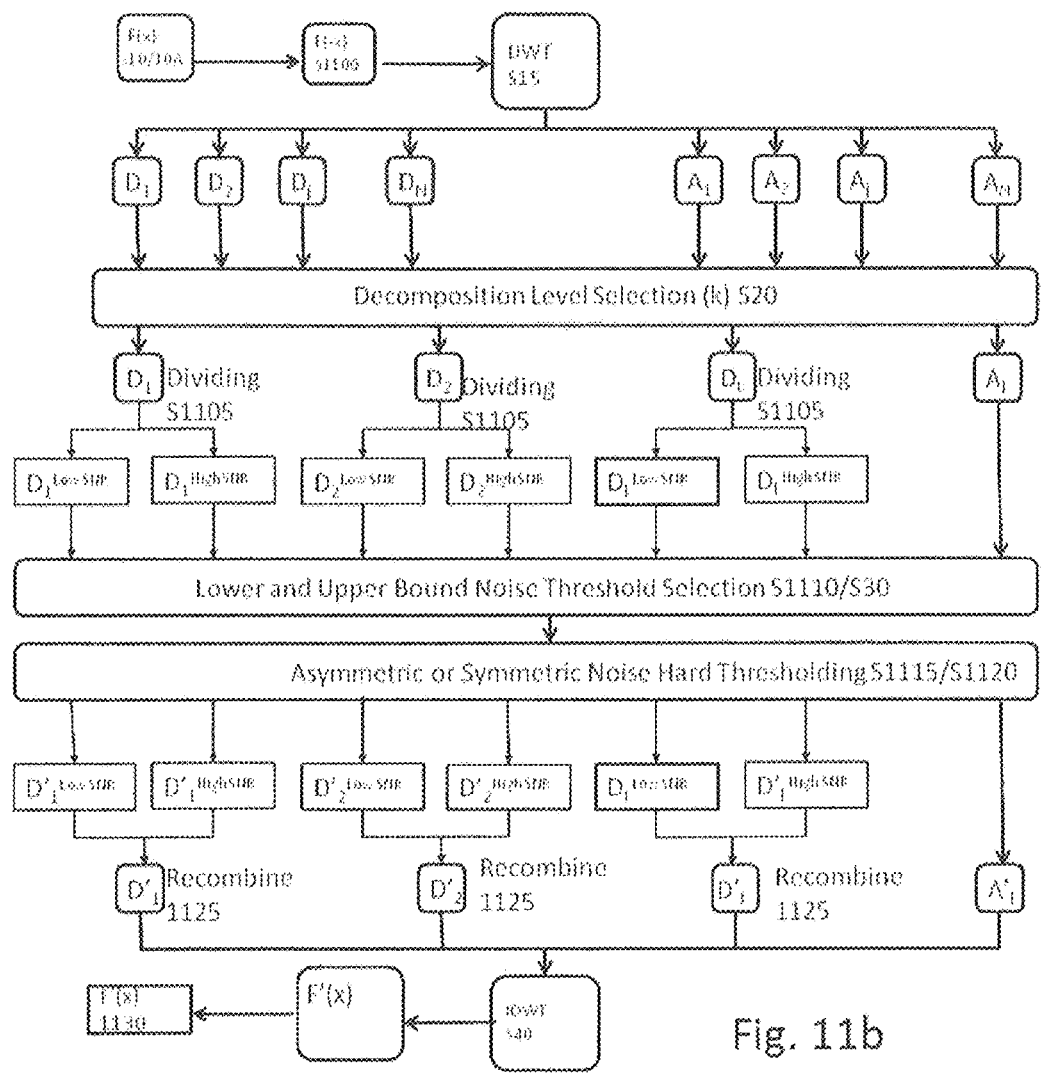

FIG. 11a depicts a flow chart of another method of denoising signals in accordance with aspects of the disclosure. FIG. 11b depicts a diagram of the method including the detail and approximation components in full scale N, divided detail components based on SNR for each of the determined decomposition levels 1-k, high/low SNR thresholding and recombination of detail components.

The denoising method depicted in FIGS. 11a/11b and FIG. 1a/1b have similar features such as, but not limited to: selection and application of a wavelet to transform, the selection of the maximum decomposition level needed to denoise the detail components based on coefficient values of at least two detail component levels, using variable thresholds, having a lower and upper threshold value, where the lower threshold is used for negative coefficients and the upper threshold is used for positive coefficients and thresholding the kth approximation component (each of the coefficients). In addition, the denoising method depicted in FIGS. 11a/11b, prior to transformation, reverses the signal and divides the detail components used for denoising into two parts high SNR and low SNR.

Common features that were described above in detail will not be described again.

As described above, at S10, the signal is acquired either via a sensor or retrieved from memory or the signal is received via a network interface over a communication network S10A. The signal is identified in FIG. 11b as F(x).

Once the signal is either acquired either via a sensor or retrieved from memory (S10) or received via the network (S10A), the processor reverses the signal at S1100. The reversed signal is identified in FIG. 11B as F(−x). For example, the signal may be flipped from left to right in the x-axis. If the signal is a time-based signal, the reversal of the signal, reverses the signal-in-time before taking the DWT. Thus, the last sample point become the first sample point and vice versa. This is done to avoid distorting the initial (e. g., t=0) signal that may occur when a signal starts at a high value and decreases over the x-axis, e.g., time.

For example, reversing the signal may result instead in having small, near-zero, magnitudes at the start, allowing more accurate DWT of the stronger part of the signal, e.g., initial response. The DWT of the flipped signal contains the same information as that of the non-flipped signal.

The processor then transforms the reversed signal using preset wavelets into both detail (first set of components) and approximation (second set of components) (S15). The detail components ($D_1$-$D_N$) and approximation components ($A_1$-$A_N$) are shown as the output of the DWT in FIG. 11b.

At S20, the processor determines the number of decomposition levels as described above. The detail components in the set decomposition level k, i.e., $D_1$-$D_k$, are shown in FIG. 11b as being output of S20. $A_k$ is also output.

For each of the determined decomposition levels used for denoising, at S1105 the processor divides the detail component into High SNR and low SNR.

In an aspect of the disclosure, the division is based on a SNR threshold. The processor may determine an SNR for each sample point in the signal (in the signal domain). Based on the determined SNR at each sample point, the processor determines the SNR threshold. The processor then compares the determined SNR at each sample point with the SNR threshold. If higher, the processor determines the sample point to be "high SNR", whereas if lower (or equal), the processor determines the sample point to be "low SNR". The correlation between a sample point and one or more coefficients in the detail component is known in view of the transformation. Therefore, the processor, based on the decision of high SNR or low SNR for each sample point in the signal, determines the corresponding coefficient(s) in the detail component and divides the coefficients into high SNR or low SNR. Coefficients that correspond to sample points determined to be high SNR, will be deemed high SNR and coefficients that correspond to sample points determined to be low SNR, will be deemed low SNR. Coefficients deemed high SNR and coefficients deemed low SNR will be separately processed for thresholding.

In another aspect of the disclosure, the SNR threshold may be based on a location within the signal. For example, the location in the middle of the signal may be used as the dividing point such that sample points left of the middle is deemed high SNR and sample points right of middle is low SNR (or vice versa). For example, if the signal is a time based signal of 6 μsec, the SNR threshold may be 3p sec. Sample points between 0-3 μsec may be deemed high SNR and sample points between 3 μsec-6 μsec may be deemed low SNR (including exactly 3 μsec). Once again, since the correlation between a sample point and one or more coefficients in the detail component is known, high SNR coefficients and low SNR coefficients may be determined from the high SNR sample points and low SNR sample points. In another aspect of the disclosure, the division may be based on the reversed signal.

Depending on the signal type and data, sample points near each other or grouped together may have a similar SNR. However, in certain types of signals and certain data collections, similar SNR sample point may be scattered throughout the signal.

For a time based signal, although the noise content is the same, the higher SNR part in earlier times may contain a signal that is less affected by noise, while noise tends to be dominant in the low SNR part. Therefore, the number of detail coefficients to denoise may different for both.

Advantageously, by separating the detail component into lower and higher SNR parts avoids an overlap between the signal wavelet coefficients of the higher SNR part and the noise wavelet coefficients of the lower SNR part, preventing under-denoising or signal distortion.

The division is repeated for 1-k decomposition levels. In FIG. 11b, the divided coefficients are identified as $D_1^{Low\ SNR}$ and $D_1^{High\ SNR}$-$D_k^{Low\ SNR}$ and $D_k^{High\ SNR}$.

At S1110, the processor determines the thresholds for thresholding for each decomposition level. As noted above, coefficients grouped in the low SNR are separately thresholded from the coefficients grouped in the high SNR. Therefore, the processor separately determines the lower and upper thresholds for coefficients grouped in the low SNR and coefficients grouped in the high SNR. For example, the processor determines a lower threshold ($\lambda_{1,LLowSNR}$) and an upper threshold ($\lambda_{1,HLowSNR}$) for $D_1^{Low\ SNR}$ and the processor separately determines a lower threshold ($\lambda_{1,LHighSNR}$)

and an upper threshold ($\lambda_{1,HHighSNR}$) for $D_1^{High\ SNR}$. As noted above, the lower threshold and the upper threshold is also separately determined.

The determination of a lower threshold and an upper threshold was described above (and shown in FIG. 3) and will not be described again in detail. However, the equations are modified based on the number of coefficients in each group of Low SNR and High SNR. For example, as described above, equations 11 and 12 use $N_j$ which is the number of coefficients in the detail component for the decomposition level. But since the number of coefficients in each group is less then $N_j$, the summations in equations 11 and 12 are with respect to the number of coefficients in each group. Similarly, $\mu_j$ and $\sigma_j$ which are the mean and standard deviation of the coefficients for the detail component, would be modified to be the mean and standard deviation of the coefficients in each group (low SNR and high SNR) in equations 7-10.

Equations 11-16 are also modified to reflect the division of detail components into the low SNR and high SNR. For example, equation 11 is used to determine the peak-to-sum ratio for the negative coefficients. However, since the detail components are divided, two peak-to-sum ratios for the negative coefficients are determined, one for the low SNR and one for the high SN, e.g., $S_{j,LLowSNR}$, $S_{j,LHighSNR}$. The peak-to-sum ratio for the negative coefficients with low SNR is determined from only the negative coefficients with the low SNR and the peak-to-sum ratio for the negative coefficients with the high SNR is determined from only negative coefficients with the high SNR.

Equation 12 used to determine the peak-to-sum ratio for the positive coefficients. However, since the detail components are divided, two peak-to-sum ratios for the positive coefficients are determined, one for the low SNR and one for the high SN, e.g., $S_{j,HLowSNR}$, $S_{j,LHighSNR}$. The peak-to-sum ratio for the positive coefficients with low SNR is determined from only the positive coefficients with the low SNR and the peak-to-sum ratio for the positive coefficients with the high SNR is determined from only positive coefficients with the high SNR.

Similarly, there are two upper and lower reference peak-to-sum ratios, $S_{r,LLowSNR}$, $S_{j,LHighSNR}$ and $S_{r,HLowSNR}$, $S_{j,LHighSNR}$, which are determined my modifying equations 13-14 to account for the division. Since equations 13 and 14 use the peak-to-sum ratio for the k+1 decomposition level, in an aspect of the disclosure, the processor also divides the detail component for the k+1 decomposition level into a low SNR and High SNR coefficients in the same manner as described above.

For example, equation 13 is modified as follows:

$$S_{r,HLowSNR} = (S_{k,HLowSNR} + S_{k+1,HLowSNR})/2 \quad (13a)$$

$$S_{r,HHighSNR} = (S_{k,HHighSNR} + S_{k+1,HHighSNR})/2 \quad (13b)$$

For example, equation 14 is modified as follows:

$$S_{r,LLowSNR} = (S_{k,LLowSNR} + S_{k+1,LLowSNR})/2 \quad (14a)$$

$$S_{r,LHighSNR} = (S_{k,LHighSNR} + S_{k+1,LHighSNR})/2 \quad (14b)$$

Also, two kappa lower and uppers are also determined: $\kappa_{j,L_{LowSNR}}$ $\kappa_{j,L_{HighSNR}}$ and $\kappa_{j,H_{LowSNR}}$ $\kappa_{j,H_{HighSNR}}$. The kappas are determined using the following modified equations 15 and 16:

$$k_{j,L_{LowSNR}} = \left(\frac{S_{r,LLowSNR} - S_{j,LLowSNR}}{S_{r,LLowSNR}}\right) k_{j,L_{minLowSNR}} \quad (15a)$$

$$k_{j,L_{HighSNR}} = \left(\frac{S_{r,LHighSNR} - S_{j,LHighSNR}}{S_{r,LHighSNR}}\right) k_{j,L_{minLowSNR}} \quad (15b)$$

$$k_{j,H_{LowSNR}} = \left(\frac{S_{r,HLowSNR} - S_{j,HLowSNR}}{S_{r,HLowSNR}}\right) k_{j,H_{minLowSNR}} \quad (16a)$$

$$k_{j,H_{HighSNR}} = \left(\frac{S_{r,HHighSNR} - S_{j,HHighSNR}}{S_{r,HHighSNR}}\right) k_{j,H_{minHighSNR}} \quad (16b)$$

The process is repeated for each of the determined decomposition levels, e.g., 1-k. For example, the processor determines a lower threshold($\lambda_{2,LLowSNR}$) and an upper threshold ($\lambda_{2,HLowSNR}$) for $D_2^{Low\ SNR}$ and the processor separately determines a lower threshold ($\lambda_{2,LHighSNR}$) and an upper threshold ($\lambda_{2,HHighSNR}$) for $D_2^{High\ SNR}$ . . . through lower threshold ($\lambda_{k,LLowSNR}$) and an upper threshold ($\lambda_{k,HLowSNR}$) for $D_k^{Low\ SNR}$ and a lower threshold ($\lambda_{k,LHighSNR}$) and an upper threshold ($\lambda_{k,HHighSNR}$) for $D_k^{High\ SNR}$.

The process is repeated for each of the determined decomposition levels, e.g., 1-k. For example, the processor determines a lower threshold and an upper threshold for $D_2^{Low\ SNR}$ and the processor separately determines a lower threshold and an upper threshold for $D_2^{High\ SNR}$ . . . through lower threshold and an upper threshold for $D_k^{Low\ SNR}$ and a lower threshold and an upper threshold for $D_k^{High\ SNR}$.

The processor also determines the lower threshold and the upper threshold for the kth approximation component at S30. The determination of a lower threshold and an upper threshold was described above (and shown in FIG. 3).

At S1115, the processor performs thresholding of the detail components in each of the low SNR and high SNR (for each determined decomposition level) using equation 17 but substituting the different thresholds for the grouping. The processor separately processes coefficients in the Low SNR and the coefficients in the high SNR using the corresponding set of $\lambda_{j,L}$ $\lambda_{j,H}$. For example, the processor will compare the value of each negative coefficient (in the Low SNR group) with $\lambda_{j,L\ LOWSNR}$ and each positive coefficient (in the Low SNR group) with $\lambda_{j,\ HLOWSNR}$. Similarly, the processor will compare the value of each negative coefficient (in the High SNR group) with $\lambda_{j,L\ HIGHSNR}$ and each positive coefficient (in the Low SNR group) with $\lambda_{j,HHIGHSNR}$. Thus, for each decomposition level instead of two thresholds there are four. $\lambda_{j,L\ LOWSNR}$, $\lambda_{j,\ HLOWSNR}$, $\lambda_{j,L\ HIGHSNR}$ and $\lambda_{j,HHIGHSNR}$. For example, positive coefficients (in the Low SNR) having a value less than or equal to $\lambda_{j,HLOWSNR}$ may be modified by the processor to zero. For example, negative coefficients (in the Low SNR) having a value greater or equal to $\lambda_{j,L\ LOWSNR}$ may be modified by the processor to zero.

FIG. 11b shows the output of S1115 being the denoised detailed components $D'_1^{LowSNR}$-$D'_1^{HighSNR}$ through $D'_k^{LowSNR}$-$D'_k^{HighSNR}$.

At S1120, the processor applies the lower threshold and the upper threshold to each coefficient in the kth approximation component. S1120 is the same as S35. The denoised approximation component is identified in FIG. 11b as $A'_k$.

At S1125, the processor recombines the denoised coefficients (modified) from both the low SNR and high SNR, to result in a denoised detail component. For example, the processor may merge the two groups together to create the denoised detail component. The denoised detail component is identified in FIG. 11b as "recombine" $D'_1$-$D'_k$.

Similar to above, prior to S40, the denoised detail components $D'_1^{LowSNR}$-$D'_1^{HighSNR}$-$D'_k^{LowSNR}$-$D'_k^{HighSNR}$ and denoised approximation component A'$_k$ can be displayed on a display side-by-side with the corresponding D$_1^{Low\ SNR}$ and D$_1^{High\ SNR}$-D$_k^{Low\ SNR}$ and D$_k^{High\ SNR}$ and approximation component A$_k$. A user can visually compare the denoised components with the corresponding noised components and adjust κ$_{j,L}$ and κ$_{j,H}$ for each of the Low SNR and High SNR based on the comparison.

At S40, the processor performs an inverse discrete transformation to recover a denoised reversed signal (shown in FIG. 11b as F'(−x) using the denoised (modified) detail components from each of the decomposition levels and the denoised (modified) approximation component at decomposition level k.

At S1130, the processor unreverses the denoised reversed signal to recover a denoised signal. For example, the processor flips the denoised reversed signal from right to left. For example, if the original signal was a time-based signal, the "unreversing" put the signal back to its original timing.

Testing and Comparison to Other Methods

The denoising method illustrated in FIGS. 11a and 11b was tested using a signal generated from a pulse-dipolar electron-spin resonance spectroscopy. A pulse-dipolar electron-spin resonance spectroscopy generates time-domain signals. These time-domain signals representing the dipolar interaction between two electron spin labels is converted into their distance distribution function P(r), usually by regularization methods such as Tikhonov Regularization.

PDS is a powerful biophysical method for the study of the structure and function of biological systems. PDS may be applied to proteins and protein complexes, which either possess endogenous paramagnetic centers or engineered sites to which paramagnetic tags (spin-labels) are covalently attached. PDS may measure the strength of the magnetic dipole-dipole interaction between electron spins usually carried by the attached spin-labels.

The signal was generate from PDS of a doubly spin-labeled cysteine mutants of T4 Lysozyme (T4L).

The signal S(t) an ensemble of proteins with two spin labels each is given as $$\int_{R_{min}}^{R_{max}} \kappa(r, t)P(r)dr = S(t) \quad (21)$$

where κ(r, t) represents an orientationally averaged signal from a spin-pair at a given r, P(r) is the distribution in distance between the spin pairs, and S(t) is the PDS signal.

Figure 25:
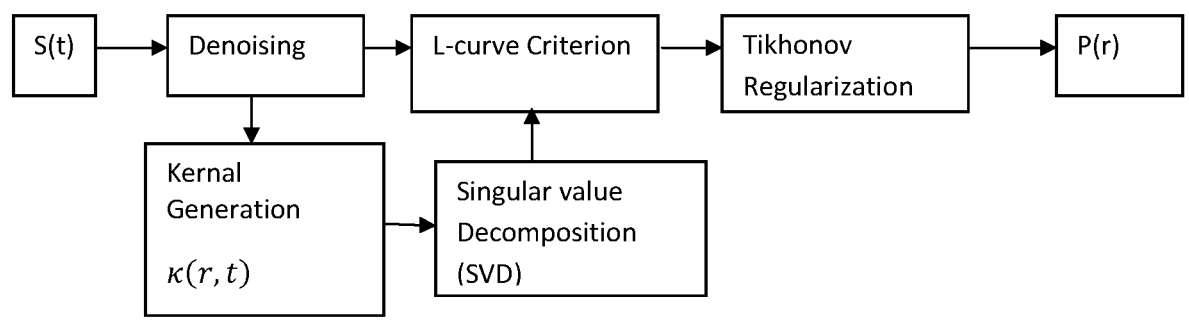
FIG. 25 depicts a method for obtaining P(r).

P(r) may be obtained as shown in FIG. 25.

A db6 wavelet from the Daubechises wavelet family was used. This wavelet correlates very well with the signal properties of decaying oscillatory time-domain signals. This results in effective separation of signal and noise by increasing the difference between their wavelet coefficient patterns.

The testing was done at 17.3 GHz and were conducted on several samples of double cysteine mutants of bacteriophage T4 lysozyme (T4L) spin-labeled with MTSL ((1-Oxyl-2,2,5,5-tetramethyl-D3-pyrroline-3-methyl) Methanethiosulfonate). These T4L mutants were generated by site-directed mutagenesis using the Quick-Exchange Multi Site-Directed Mutagenesis Kit (Agilent Technologies, Stratagene Products Division), expressed in *E. coli* BL21(DE3) cells, and purified and spin-labeled.

After spin-labeling and removal of unreacted MTSL, the protein concentration was determined from the UV absorbance at 280 nm. The following samples of spin-labeled T4L were studied: (i) SAMPLE 1—63 μM of mutant 44 C/135 C;

(ii) SAMPLE 2—mixture of mutants 8 C/44 C and 44 C/135 C at concentrations of 44 μM and 47 μM, respectively. In both cases, the buffer composition was—25 mM Tris/25 mM MOPS pH 7.6, 1 mM EDTA and 10% Gly (w/v); before freezing for PDS measurements, an extra 20% Gly-d8 (w/v) was added to the samples. The protein concentrations given above are those before the extra 20% Gly-d8.

Four-pulse double electron-electron resonance (DEER) measurements at 17.3 GHz and 60 K were performed using a home-built Ku-band pulse spectrometer under standard experimental conditions. The spectrometer was tuned-up by using both the primary and refocused echoes, which are much stronger than the DEER signal. The π/2-π-π DEER pulse widths were 16 ns, 32 ns and 32 ns, respectively, and the it pump pulse was 32 ns. A frequency separation of 70 MHz between detection and pump pulses was used. The detection pulses were applied at the low-field edge and the pump pulse was positioned near the center of nitroxide spin-label spectrum, close to the maximum. DEER time-domain signals of 4-5 μs dipolar evolution times were collected. Three data-sets at different DEER signal averaging times were produced for each sample, resulting in widely different SNR. From these time-domain DEER data, inter-spin distance distributions were reconstructed using TIKR and refined by Maximum Entropy method (MEM) to constrain P(r)≥0. Since SAMPLE 1 contained just one doubly spin-labeled protein mutant, it produced a unimodal distance distribution, whereas SAMPLE 2 produced a bimodal distance distribution due to the superposition of two unimodal distributions.

Kernal generation, SVD, L-curve criterion and TIKR are described in Chiang, Y.-W.; Borbat, P. P.; Freed, J. H. The Determination of Pair Distance Distributions by Pulsed ESR Using Tikhonov Regularization. *J. Magn. Reson.* 2005, 172 (2), 279-295, which is incorporated herein by reference. MEM is described in Chiang, Y.-W.; Borbat, P. P.; Freed, J. H. Maximum Entropy: A Complement to Tikhonov Regularization for Determination of Pair Distance Distributions by Pulsed ESR. *J. Magn. Reson.* 2005, 177 (2), 184-196, which is incorporated by reference.

Signals generating for Sample 1 was signal-averaged for three different acquisition periods generating small, medium, and large SNRs: 14, 112 and 952 minutes. Denoising was applied after the baseline was subtracted from the original signals. However, denoising may be perform before baseline subtraction which may include in the removal of noisy signals.

Figures 12A, 12B, 12C:
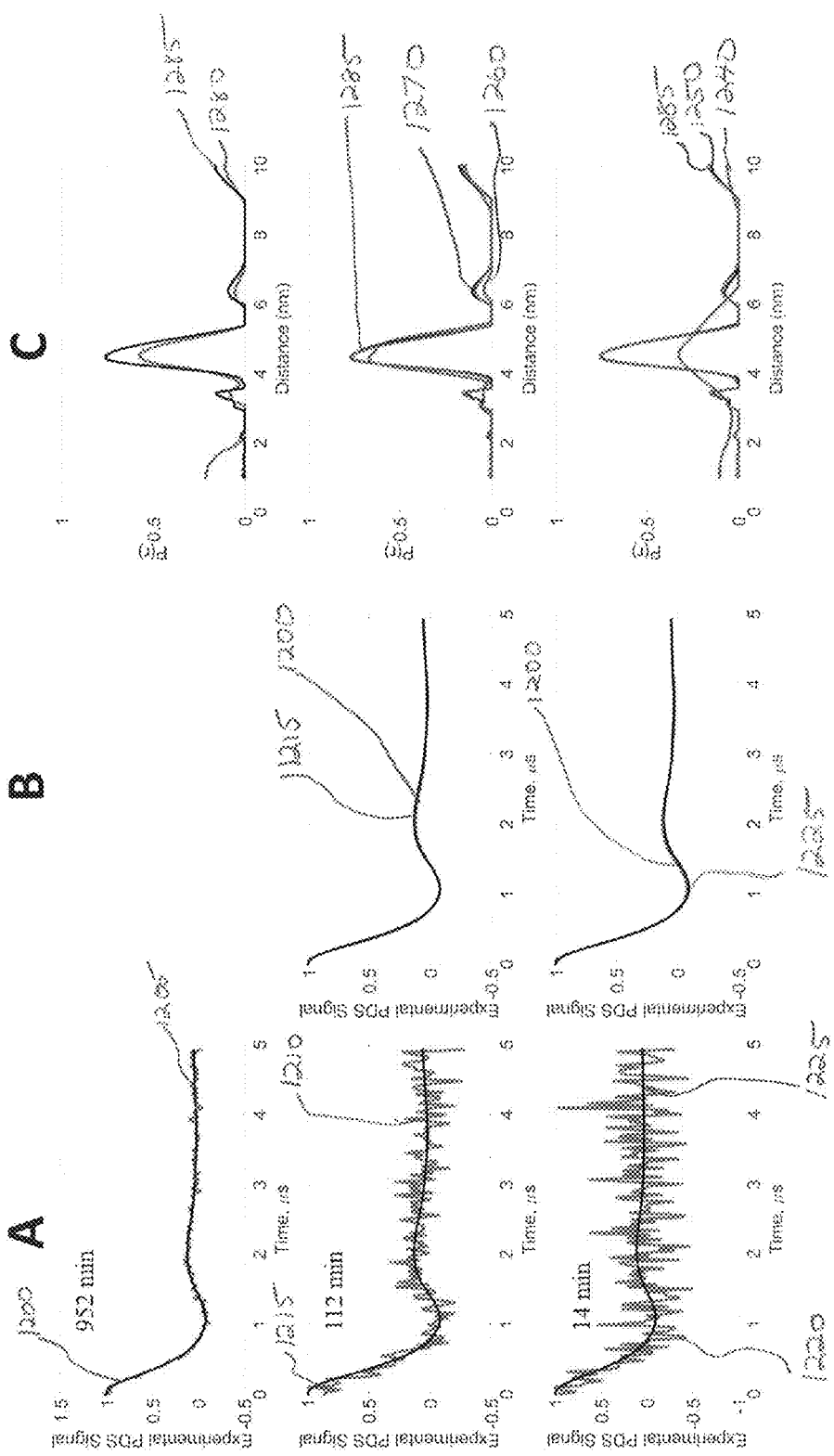
FIGS. 12a-12c depict test results for Sample 1 denoised in accordance with the denoising method depicted in FIGS. 11a and 11b.

FIG. 12a illustrates the test results for sample 1 over the three different average periods. Each chart reflects the results for a specific average period. The top is for 952 mins (noisy signal is identified as "1205"); the middle is for 112 min (noisy signal is identified as "1210" and the denoised signal is identified as "1215"); and the bottom is for 14 mins (the noisy signal is identified as "1220" and the denoised signal is identified as "1225). The different average periods generated different SNRs. Each chart in "A" has a noisy signal and a denoised signal using the denoising method as described above. The reference signal is identified as "1200".

FIG. 12b illustrates a comparison of a reference signal with the denoised signal (sample 1). The denoised signal at 952 mins was used as the reference ("1200"). Thus, the top of FIG. 12b ("B") is a comparison of the denoised signal 112 mins (1215) and the reference signal (1200) and the bottom is a comparison of the denoised signal 14 mins (1225) and the reference signal (1200).

FIG. 12c illustrates the distance distributions P(r) from Noisy, Denoised (using the denoising method depicted in FIGS. 11a and 11b) and reference signals (sample 1). The top shows the result P(r) determined from the noisy signal (identified as "1280") and the P(r) determined from the denoised (reference signal) identified as "1285".

As seen in FIG. 12c, a mild sharpening up of the P(r) is observed after applying the denoising method as depicted in FIGS. 11a and 11c (shown by an increase in the peak, the difference being indicated by the different peak between the lower curve (noisy signal) and the upper curves (denoised and reference signal) in both the middle and lower chart). Most of the residual noise has been removed in the denoised time-domain signal. The middle chart (112 mins acquisition) shows P(r) determined from the noisy signal identified as "1260", P(r) determined from the denoised signal identified as 1270 and P(r) determined from the reference signal 1285. The bottom chart (14 mins acquisition) shows P(r) determined from the noisy signal identified as "1240", P(r) determined from the denoised signal identified as 1250 and P(r) determined from the reference signal 1285.

Since a signal with a good SNR was achieved after 952 min, it was use in its denoised form as the reference to compare with the cases of reduced acquisition time.

When the signal acquisition time is reduced by almost an order of magnitude (from 952 to 112 min) the noise increases significantly but the denoised signal and P(r) are almost identical to the reference as seen in FIG. 12b and FIG. 12c. As seen in the P(r) from FIG. 12c, the P(c) determined from the denoised signal and the reference signal is almost indistinguishable in the middle and lower charts (upper two curves). In contrast, the results from the noisy data is not the same as seen in Table 4 (for example looking at the SSIM values and the $\chi^2$ (0.190 and 0.135, respectively).

$$\chi^2 \equiv \sqrt{\frac{1}{p}\sum_{i=1}^{P}(Y[i] - X[i])^2} \quad (22)$$

where X and Y are input and reference signals, respectively.

A reduction of signal averaging time from 112 mins to 14 mins further highlights the significant improvement over the noisy signal. This yields a very noisy signal that is too noisy for a P(r) to be recovered using $\lambda_{TIKR}$, but the result shown in FIG. 12c is for $\lambda_{TIKR}^{OPT}$ and is too broad. In contrast, using the denoised signal, nearly identical results may be achieved with respect to the reference.

Additionally, as can be seen in the Table 4, the SNR of the noisy signal dramatically improved after being denoising according to the denoising method depicted in FIGS. 11a and 11b, e.g., 6.8→909. Further, the $\chi^2$ and SSIM of the denoised signal also significantly improved, e.g 0.190→0.0011 and 0.135→0.995.

TABLE 4

Comparison of Noisy v. denoised signal with respect to the reference signal. The SNR in the above table is not in dbs

| | SNR | $\chi^2$ | SSIM |
|---|---|---|---|
| Noisy → Denoised | 37 → (Reference) | 0.027→ 0 (Reference) | 0.676 → 1 (Reference) |
| | 6.8 → 909 | 0.190 → 0.0011 | 0.135 → 0.995 |
| | 3.8 → 488 | 0.263 → 0.0021 | 0.038 → 0.967 |

Figures 13A, 13B, 13C:
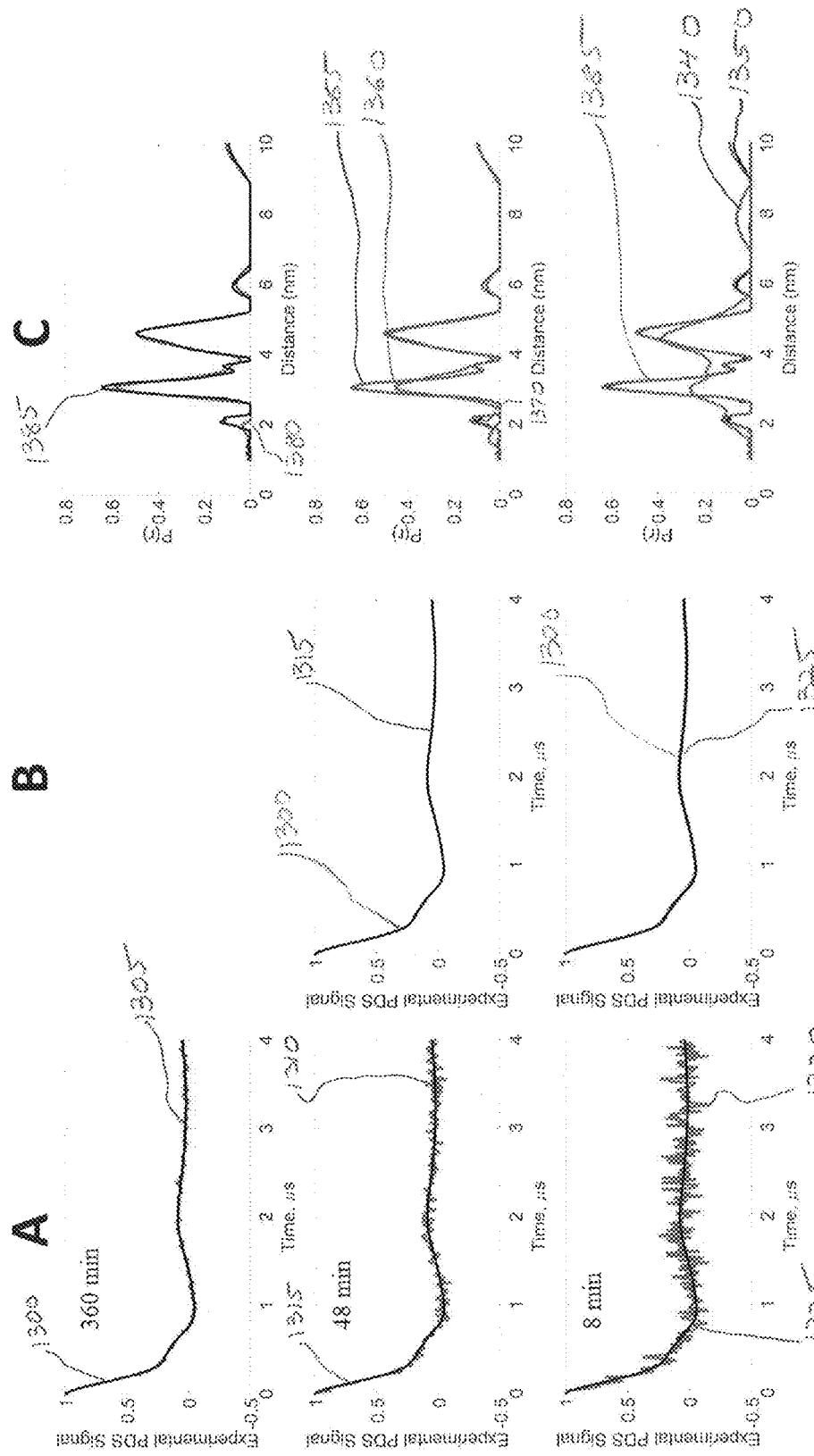
FIGS. 13a-13c depict test results for Sample 2 denoised in accordance with the denoising method depicted in FIGS. 11a and 11b.

FIG. 13a illustrates the test results for sample 2 over three different average periods. Each chart reflects the results for a specific average period. The top is for 360 mins (noisy signal is identified as "1305" and denoised signal is identified as 1300 (which is also the reference signal); the middle is for 48 min (noisy signal is identified as "1310" and the denoised signal is identified as "1315"); and the bottom is for 8 mins (noisy signal is identified as "1320" and denoised signal is identified as "1325"), generating different SNRs. Each chart has a noisy signal and a denoised signal using the denoising method as depicted in FIGS. 11a and 11b.

FIG. 13b illustrates a comparison of a reference signal with the denoised signal (sample 2). The denoised signal at 360 mins was used as the reference, 1300. Thus, the top of FIG. 12b is a comparison of the denoised signal 48 mins (1315) and the reference signal (1300) and the bottom is a comparison of the denoised signal 8 mins (1325) and the reference signal (1300).

FIG. 13c illustrates the distance distributions P(r) from Noisy, Denoised and reference signals (sample 2) for each of the different acquisition periods. The top shows the result P(r) determined from the noisy signal (identified as "1380") and the P(r) determined from the denoised (reference signal) identified as "1385').

The middle chart (48 mins acquisition) shows P(r) determined from the noisy signal identified as "1360", P(r) determined from the denoised signal identified as 1370 and P(r) determined from the reference signal 1385. The bottom chart (8 mins acquisition) shows P(r) determined from the noisy signal identified as "1340", P(r) determined from the denoised signal identified as 1350 and P(r) determined from the reference signal 1385.

TABLE 5

Comparison of Noisy v. denoised signal with respect to the reference signal. The SNR in the above table is not in dbs.

| | SNR | $\chi^2$ | SSIM |
|---|---|---|---|
| Noisy → Denoised | 80 → (Reference) | 0.013 → 0 (Reference) | 0.8815 → 1 (Reference) |
| | 31 → 3333 | 0.032 → 0.0003 | 0.573 → 0.999 |
| | 11 → 1046 | 0.086 → 0.0009 | 0.156 → 0.961 |

As seen in FIGS. 13a-13c the noisy signal at 360 min is nearly noiseless, so the "noisy" and denoised P(r) are very similar. SNR of the noisy signal was 80. Accordingly, the denoised signal at 360 min (denoised according to the method depicted in FIGS. 11A and 11B) was taken as the reference for the bimodal signals.

As seen in FIG. 13c (middle chart), the 48 min noisy signal, the distance distribution is able to retrieve the two peaks but the first peak is appears smaller and broader than the second peak. In contrast, using the denoised signal (still at 48 min), both peaks can be retrieved.

As seen in FIG. 13c (bottom chart), for 8 min, the noisy signal yields a very broad P(r) that is barely able to reveal the existence of two peaks. In contrast, the denoised signal at 8 min is successfully able to retrieve the two peaks, and it is very nearly identical to the reference.

Additionally, as can be seen in Table 5, the SNR of the noisy signal dramatically improved after being denoising according to the denoising method depicted in FIGS. 11a and 11b, e.g., 31→3333. Further, the $\chi^2$ and SSIM of the denoised signal also significantly improved, e.g., 0.032→0.0003 and 0.573→0.999, respectively.

In fact, as seen in both Tables 4 and 5, the SNR of the time-domain signal is increased by a factor of about 100.

Also, looking at both Tables 4 and 5, show that the denoising method accurately reflects the signal as demonstrated by the SSIM value.

Table 6 shows a comparison of the denoising method depicted in FIGS. 11a and 11b with conventional Denoising methods (Minimax and SUREShrink) on Sample 1 at acquisition time 14 min (average).

λ is the regularization parameter. The optimal λ is referenced in the table as $\lambda^{OPT}_{TIKR}$. $\lambda^{L\text{-}Curve}_{TIKR}$ is the regularization parameter determined using the L-curve method.

| Method | SNR | $\chi^2$ | SSIM | $\lambda^{OPT}_{TIKR}$ | $\lambda^{L\text{-}Curve}_{TIKR}$ |
|---|---|---|---|---|---|
| Noisy | 3.8 | 0.263 | 0.038 | 30 | 0.08 |
| Minimax-Hard | 6 | 0.160 | 0.386 | 10 | 28 |
| Minimax-Soft | 13 | 0.079 | 0.306 | 10 | 4 |
| SUREshrink-Hard | 7 | 0.142 | 0.288 | 10 | 24 |
| SUREshrink-Soft | 11 | 0.094 | 0.313 | 10 | 26 |
| FIGS. 11A and 11B | 488 | 0.0021 | 0.967 | 0.08 | 0.08 |

As can be seen from Table 6, the denoising method significantly increased the SNR of the denoised signal as compared with conventional denoising methods.

Table 7 shows a comparison of the denoising method depicted in FIGS. 11A and 11B with conventional Denoising methods (Minimax and SUREShrink) on Sample 2 at acquisition time 8 min (average).

| Method | SNR | $\chi^2$ | SSIM | $\lambda^{OPT}_{TIKR}$ | $\lambda^{L\text{-}Curve}_{TIKR}$ |
|---|---|---|---|---|---|
| Noisy | 11 | 0.086 | 0.156 | 10 | 255 |
| Minimax-Hard | 19 | 0.052 | 0.418 | 8 | 46 |
| Minimax-Soft | 33 | 0.030 | 0.708 | 8 | 31 |
| SUREshrink-Hard | 15 | 0.065 | 0.266 | 8 | 119 |
| SUREshrink-Soft | 23 | 0.044 | 0.469 | 8 | 40 |
| FIGS. 11A and 11B | 1046 | 0.0009 | 0.961 | 0.09 | 0.09 |

As can be seen from Table 7, the denoising method significantly increased the SNR of the denoised signal as compared with conventional denoising methods. The conventional denoising methods only increase the SNR by a factor of 2-3, whereas the denoising method described in FIGS. 11a and 11b increase the SNR by an order of approximately 100. It appears that the conventional denoising methods are not as successful in removing the noise coefficients in the detail components representing high-frequency sub-bands nor do they remove any low-frequency noise present in the final Approximation component.

FIGS. 14a-18c depict the comparison of denoising methods for Sample 1 with 14 min of acquisition time; FIGS. 14a-14c depict the Minimax-with hard thresholding; FIGS. 15a-15c depict the Minimax-with soft thresholding; FIGS. 16a-16c depict the SUREshrink with hard thresholding; FIGS. 17a-17c depict the SUREshrink with soft thresholding and FIGS. 18a-18c depict the denosing method described in FIGS. 11a and 11b.

The "A" chart in each figure depicts the noisy signal (the noisy signal is identified as "1220" as used above) and the denoised signal (the denoised signal denoised according to the method described in FIGS. 11a/11b is identified as "1225", where the denoised signals denoised in accordance with conventional methods is identified as "1400$_{1\text{-}4}$"). The "B" chart in each figure depicts the denoised signal (1400$_{1\text{-}4}$ and 1225, respectively) and the reference signal (1200). The "C" depicts the determined P(r) from the noisy signal, the denoised signal and the reference signal. P(r) determined from the reference signal is identified as 1285 as used above). P(r) determined from the respective denoised signals is identified as 1410$_{1\text{-}4}$ (for the conventional methods) and 1250 for the P(r) determined from the denoising method as described in FIGS. 11a-11b. P(r) determined from the noisy signal is identified as 1240. The same reference was used in each figure. The denoised signal using the denoising method described in FIGS. 11a and 11v at 952 mins was used as the reference. As can be seen in FIGS. 14a/b, 15a/b, 16a/b and 17a/b, the denoised signals based on conventional methods do not correlate well with the reference signal, whereas the denoised signal in FIG. 18b matches. Moreover, and importantly, the peak P(r) determined from the denoised signals of the conventional methods does not match, the peak P(r) determined from the reference (FIGS. 14c-17c). In fact, the peaks are much lower and wider in most cases, whereas the peak P(r) determined from the denoised signal from the method disclosed in FIGS. 11a and 11b achieved almost perfect correlated with the reference (FIG. 18c).

Figures 19A, 19B, 19C, 20A, 20B, 20C, 21A, 21B, 21C, 22A, 22B, 22C, 23A, 23B, 23C:
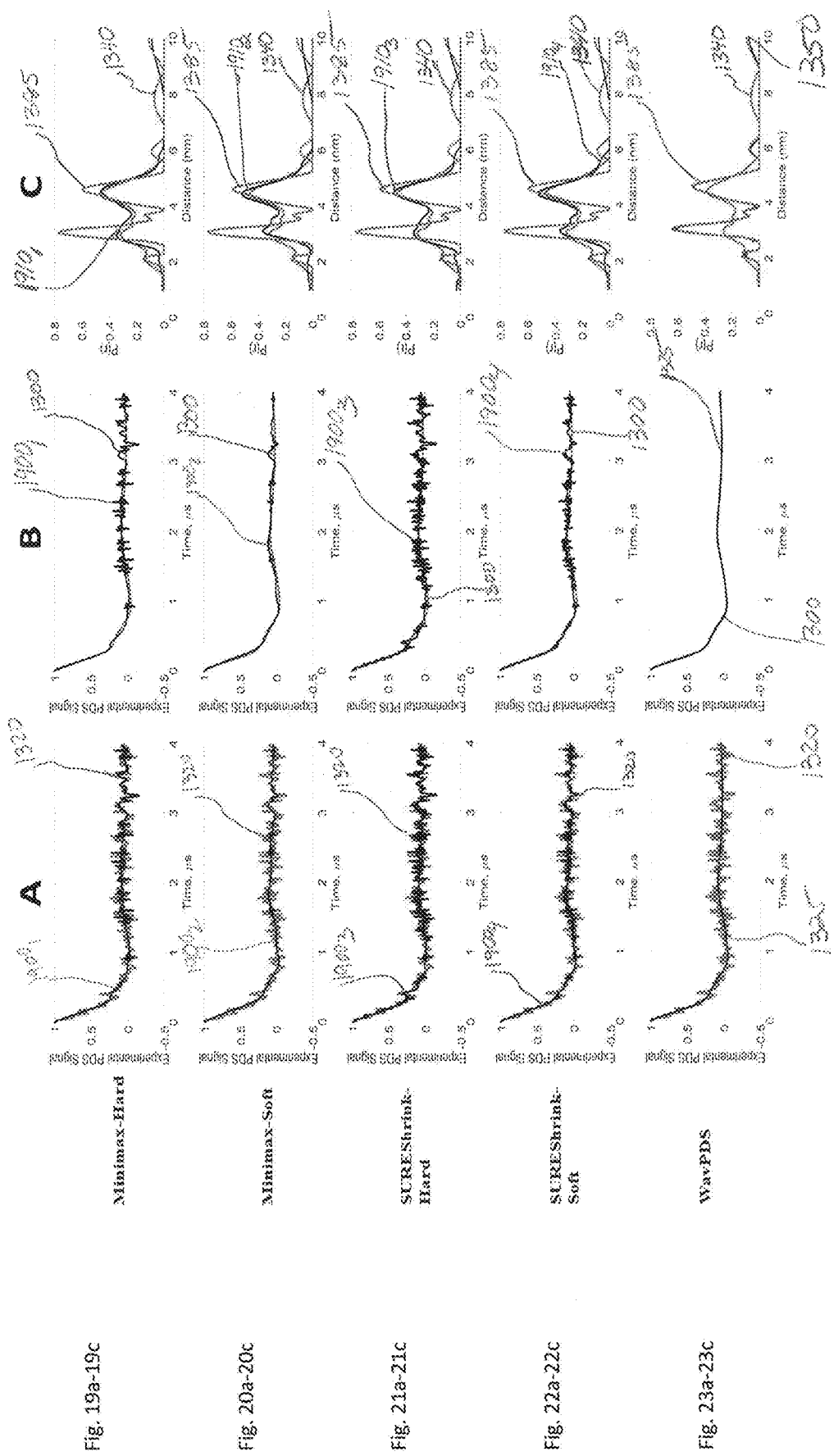

Similar results are shown for sample 2. FIGS. 19a-23c depict the comparison of denoising methods for Sample 2 with 8 min of acquisition time; FIGS. 19a-19c depict the Minimax-with hard thresholding; FIGS. 20a-20c depict the Minimax-with soft thresholding; FIGS. 21a-21c depict the SUREshrink with hard thresholding; FIGS. 22a-22c depict the SUREshrink with soft thresholding and FIGS. 23a-23c depict the denoising method described in FIGS. 11a and 11b. The "A" chart in each figure depicts the noisy signal (the noisy signal is identified as 1320 as used above) and the denoised signal (the denoised signal denoised according to the method described in FIGS. 11a/11b is identified as "1325", where the denoised signals denoised in accordance with conventional methods is identified as "1900$_{1\text{-}4}$"). The "B" chart in each figure depicts the denoised signal (1900$_{1\text{-}4}$ and 1325, respectively) and the reference signal (1300). FIGS. 23b and 23c show almost perfect correlation whereas the other figs. (FIGS. 19b/c, 20b/c, 21b/c and 22b/22c show significant differences between the two peaks from the denoised signal and the reference signal. The peaks P(r) determined from the denoised signals according to the conventional methods is lower than the peaks determined from the reference. P(r) determined from the reference signal is identified as 1385 as used above). P(r) determined from the respective denoised signals is identified as 1910$_{1\text{-}4}$ (for the conventional methods) and 1350 for the P(r) determined from the denoising method as described in FIGS. 11a-11b. P(r) determined from the noisy signal is identified as 1340.

Figures 24A, 24B:
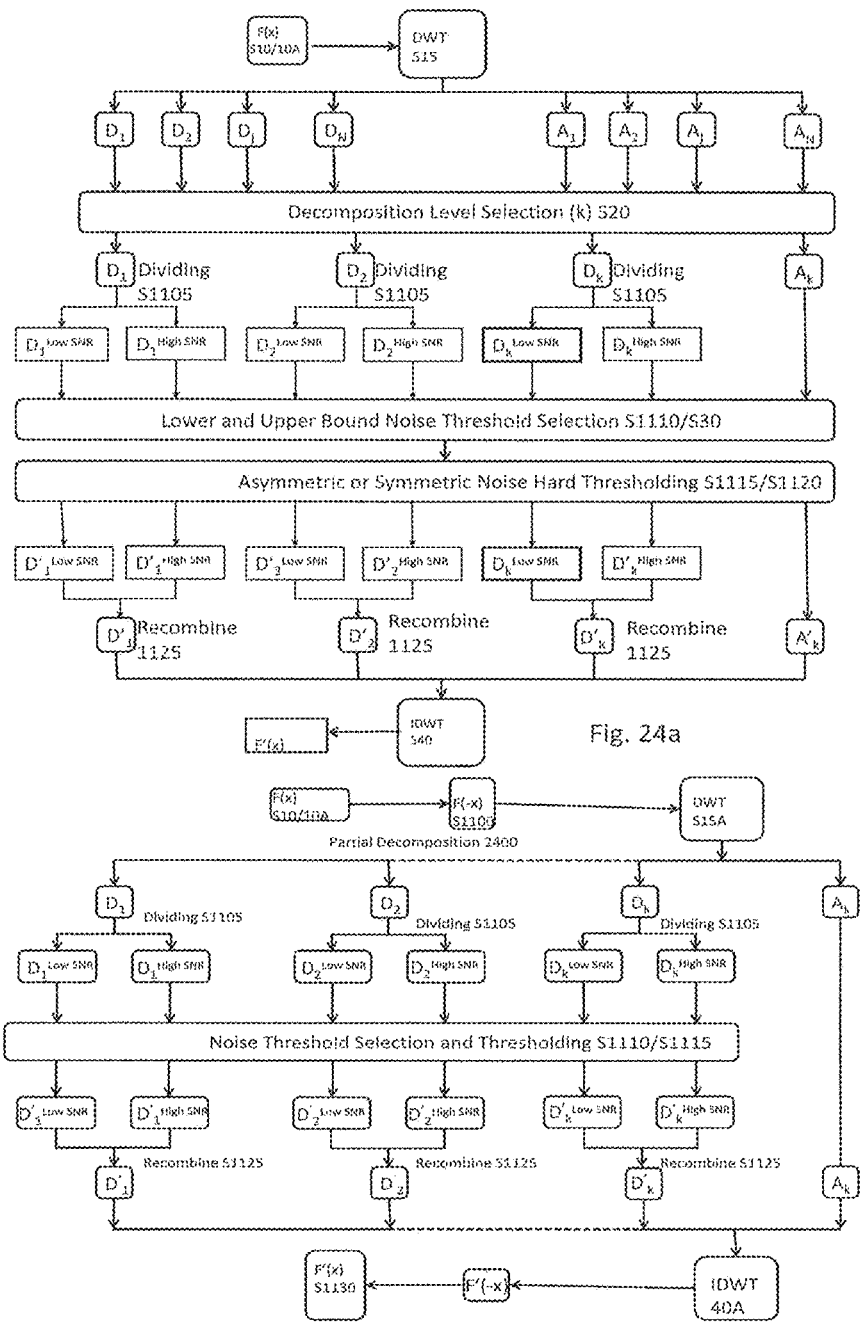
FIG. 24a depicts a diagram of another denoising method according to aspects of the disclosure.
FIG. 24b depicts a diagram of another denoising method according to aspects of the disclosure.

In another aspect of the disclosure, depending on the type of signal, the application and properties on the signal, reversing the signal may be omitted from the method depicted in FIGS. 11a and 11b. For example, if the signal does not exhibit a large initial value with decay over the x-axis, e.g., time, the reversal of the signal may be omitted. FIG. 24a depicts a denoising method in accordance with aspects of the disclosure with the reversal omitted. Except for the removal of the reversing the signal and unreversing, the denoising method depicted in FIG. 24a is the same as the denoising method in FIGS. 11a and 11b and therefore will not be described again in detail.

In another aspect of the disclosure, depending on the type of signal, the application and properties on the signal, thresholding of the kth approximation component may be omitted.

Additionally, an objective determination of the number of decomposition levels used for thresholding may also be omitted and replaced with a random determination prior to DWT. Therefore, instead of a DWT which initial produces a fully scale decomposition of both the detail components and approximation component "N", the DWT may only generate k different levels of detailed components and the kth level of approximation component. FIG. 24b depicts a denoising method in accordance with aspects of the disclosure with the objective determination of the number of decomposition levels, fully scale decomposition and approximation thresholding omitted. In FIG. 24b, the DWT S15A transforms the signal into the k different levels of detail components ($D_1$-$D_k$) and kth approximation ($A_k$) (referred to as partial decomposition 2400 as opposed to full scale). S20, S30 and S1120 are omitted from the method depicted in FIG. 24b. Since the approximation component is not denoised or modified, the inverse transformation 40A used the unmodified approximation component.

The remaining features of FIG. 24b are the same as described in FIGS. 11a and 11b and therefore will not be described again.

While the system 890, 900 were described herein as executing the denoising method described in FIGS. 1a and 1b, the systems 890, 900 may be configured to execute any and all of the denoising methods describe above.

Various aspects of the present disclosure may be embodied as a program, software, or computer instructions embodied or stored in a computer or machine usable or readable medium, or a group of media which causes the computer or machine to perform the steps of the method when executed on the computer, processor, and/or machine. A program storage device readable by a machine, e.g., a computer readable medium, tangibly embodying a program of instructions executable by the machine to perform various functionalities and methods described in the present disclosure is also provided, e.g., a computer program product.

The computer readable medium could be a computer readable storage device or a computer readable signal medium. A computer readable storage device, may be, for example, a magnetic, optical, electronic, electromagnetic, infrared, or semiconductor system, apparatus, or device, or any suitable combination of the foregoing; however, the computer readable storage device is not limited to these examples except a computer readable storage device excludes computer readable signal medium. Additional examples of the computer readable storage device can include: a portable computer diskette, a hard disk, a magnetic storage device, a portable compact disc read-only memory (CD-ROM), a random access memory (RAM), a read-only memory (ROM), an erasable programmable read-only memory (EPROM or Flash memory), an optical storage device, or any appropriate combination of the foregoing; however, the computer readable storage device is also not limited to these examples. Any tangible medium that can contain, or store, a program for use by or in connection with an instruction execution system, apparatus, or device could be a computer readable storage device.

A computer readable signal medium may include a propagated data signal with computer readable program code embodied therein, such as, but not limited to, in baseband or as part of a carrier wave. A propagated signal may take any of a plurality of forms, including, but not limited to, electromagnetic, optical, or any suitable combination thereof. A computer readable signal medium may be any computer readable medium (exclusive of computer readable storage device) that can communicate, propagate, or transport a program for use by or in connection with a system, apparatus, or device. Program code embodied on a computer readable signal medium may be transmitted using any appropriate medium, including but not limited to wireless, wired, optical fiber cable, RF, etc., or any suitable combination of the foregoing.

The terms "Processor", as may be used in the present disclosure may include a variety of combinations of fixed and/or portable computer hardware, software, peripherals, and storage devices. The "Processor" may include a plurality of individual components that are networked or otherwise linked to perform collaboratively, or may include one or more standalone components. The hardware and software components of the "Processor" of the present disclosure may include and may be included within fixed and portable devices such as desktop, laptop, and/or server, and network of servers (cloud).

The terminology used herein is for the purpose of describing particular embodiments only and is not intended to be limiting the scope of the disclosure and is not intended to be exhaustive. Many modifications and variations will be apparent to those of ordinary skill in the art without departing from the scope and spirit of the disclosure.

What is claimed is:

1. A method of denoising a signal comprising:
    transforming a signal using a discrete wavelet transformation into a first wavelet component and a second wavelet component for each of a plurality of different resolutions, respectively, using preset wavelets, each of the first wavelet component and the second wavelet component having a plurality of coefficients;
    determining a number of different resolutions, where the number is k, of the plurality of different resolutions for use in thresholding by examining at least coefficients for the first wavelet component for at least two of the plurality of different resolutions, respectively;
    for each of the determined number of different resolutions for use in thresholding, comparing each coefficient in the first wavelet component with a variable threshold, the variable threshold for each of the determined number of different resolutions being different, and selectively changing a value of the coefficient based on the comparison thereby generating a modified first wavelet component having changed coefficients and unchanged coefficients;
    for the kth different resolution, comparing each coefficient in the second wavelet component with a second variable threshold, and selectively changing a value of the coefficient based on the comparison, thereby generating a modified second wavelet component having changed coefficients and unchanged coefficients; and
    transforming, using an inverse discrete wavelet transformation, the modified first wavelet component for each of the determined number of resolutions and the modified second wavelet component into a denoised signal.

2. The method of denoising a signal according to claim 1, wherein k is based on a comparison of a maximum value to sum value ratio of values of the coefficients for the first wavelet component with a decomposition threshold for at least two of the plurality of different resolutions.

3. The method of denoising a signal according to claim 2, wherein the determining of k comprises:
    calculating the maximum value to sum value ratio for two different resolutions;
    comparing the maximum value to sum value ratio for the two different resolutions with the decomposition level threshold, wherein if the maximum value to sum value ratio of one of the two different resolutions is greater than the decomposition level threshold, k is determined at 2, wherein if the maximum value to sum value ratio for both different resolutions is less than or equal to the decomposition level threshold, the determining of k further comprises:

calculating the maximum value to sum value ratio for an additional different resolution and comparing the calculated the maximum value to sum value ratio for the additional different resolution with the decomposition level threshold, repeatedly, until the maximum value to sum value ratio for an additional different resolution is greater than the decomposition level threshold, and wherein when the calculated maximum value to sum value ratio for an additional different resolution is greater the decomposition level threshold, k is determined as a total number of times the maximum value to sum value ratio was calculated minus 1.

4. The method of denoising a signal according to claim 1, further comprising displaying the first wavelet component and the second wavelet component, respectively, for each of a plurality of different resolutions and wherein k is based on a visual inspection of at least the first wavelet component for a subset of the plurality of different resolutions.

5. The method of denoising a signal according to claim 1, the variable threshold comprises a lower variable threshold and an upper variable threshold.

6. The method of denoising a signal according to claim 5, the lower variable threshold is a negative value and compared to negative coefficients and the upper variable threshold is a positive value and compared to positive coefficients.

7. The method of denoising a signal according to claim 5, wherein coefficients having values between the lower variable threshold and the upper variable threshold are reduced as the change.

8. The method of denoising a signal according to claim 7, wherein the reduction is to zero.

9. The method of denoising a signal according to claim 5, further comprising:

determining the lower variable threshold for each of the determined number of different resolutions; and determining the upper variable threshold for each of the determined number of different resolutions, wherein the lower variable threshold and the upper variable threshold is separately determined.

10. The method of denoising a signal according to claim 9, wherein for each of the determined number of different resolutions for use in thresholding, the lower variable threshold is determined using an average value of the coefficients for the first wavelet component for that resolution, a standard deviation of the coefficients for the first wavelet component for that resolution and a first scaling factor for the standard deviation for that resolution, and the lower variable threshold is determined using an average value of the coefficients for the first wavelet component for that resolution, a standard deviation of the coefficients for the first wavelet component for that resolution and a second scaling factor for the standard deviation for that resolution.

11. The method of denoising a signal according to claim 10, further comprising:

displaying the first wavelet component and the second set of wavelet component, respectively, for each of a plurality of different resolutions and the modified first wavelet component for each of the determined number of different resolutions and the modified second wavelet component;

comparing, visually the first wavelet component and the modified first wavelet component for each of the determined number of different resolutions; and adjusting the first scaling factor and the second scaling factor for at least one resolution based on the comparing.

12. A method of denoising a signal comprising:

reversing in time, a signal;

transforming the time reversed signal using a discrete wavelet transformation into a first wavelet component for each of a number of different resolutions, wherein the number of different resolutions is k and a second wavelet component for the kth different resolution, each of the first wavelet component and the second wavelet component for the kth different resolution having a plurality of coefficients;

for each of the number of different resolutions, dividing coefficients for the first wavelet components into a first-subset of coefficients and a second-subset of coefficients based on a determined signal to noise ratio;

comparing each coefficient in the first-subset of coefficient with a first variable threshold, the first variable threshold for each of the number of different resolutions being different, and selectively changing a value of the coefficient in the first-subset of coefficients based on the comparison thereby generating a modified first subset of coefficients having changed coefficients and unchanged coefficients;

comparing each coefficient in the second-subset of coefficients with a second variable threshold, the second variable threshold for each of the number of different resolutions being different, and selectively changing a value of the coefficient in the second-subset of coefficients based on the comparison thereby generating a modified second subset of coefficients having changed coefficients and unchanged coefficients; and combining the modified first subset of coefficients with the second subset of coefficients, transforming, using an inverse discrete wavelet transformation, at least the combined modified first subset of coefficients and the modified second subset of coefficients for each of the number of resolutions into a reversed in time denoised signal; and reversing in time the reversed in time denoised signal to generate a denoised signal.

13. The method of denoising a signal according to claim 12, further comprising determining a threshold for dividing the first component into the first-subset of coefficients and the second-subset of coefficients for each of the number of resolutions.

14. The method of denoising a signal according to claim 12, further comprising: determining the number of different resolutions, wherein the number of different resolutions is k, wherein the determining k comprises examining at least coefficients for a set of components for at least two of a plurality of different resolutions, the set of components for the plurality of different resolutions include the first wavelet component for each of the number of different resolutions and additional first wavelet component for additional resolutions levels, the number of additional resolution levels being based on a maximum different resolution levels for the signal.

15. The method of denoising a signal according to claim 14, wherein k is based on a comparison of a maximum value to sum value ratio of values of the coefficients for the set of components with a decomposition threshold for at least two of the plurality of different resolutions.

16. The method of denoising a signal according to claim 14, wherein each of the first variable threshold and the second variable threshold, respectively for each of the number of different resolutions comprises a lower variable threshold and an upper variable threshold.

17. The method of denoising a signal according to claim 15, the lower variable threshold is a negative value and compared to negative coefficients and the upper variable threshold is a positive value and compared to positive coefficients.

18. The method of denoising a signal according to claim 16, further comprising:
determining the lower variable threshold for each of the determined number of different resolutions; and
determining the upper variable threshold for each of the determined number of different resolutions, wherein the lower variable threshold and the upper variable threshold is separately determined.

19. The method of denoising a signal according to claim 12, further comprising:
for the kth different resolution, comparing each coefficient in the second wavelet component with a third variable threshold, and selectively changing a value of the coefficient based on the comparison, thereby generating a modified second wavelet component having changed coefficients and unchanged coefficients, wherein the at least the combined modified first subset of coefficients and the modified second subset of coefficients for each of the number of resolutions further includes the modified second wavelet component.

20. The method of denoising a signal according to claim 19, further comprising determining the third variable threshold, the third variable threshold comprising a lower variable threshold and an upper variable threshold which are separately determined.

21. The method of denoising a signal according to claim 12, wherein the at least the combined modified first subset of coefficients and the modified second subset of coefficients for each of the number of resolutions further includes a second wavelet component for the kth different resolution.

22. The method of denoising a signal according to claim 12, wherein the signal is selected from a group consisting of an audio signal and a video signal, the signal being streamed over a network, the network comprising at least one source server storing the signal, one or more relay nodes and a user terminal.

23. The method of denoising a signal according to claim 22, wherein the at least one server comprises a processor configured to execute the method of denoising a signal according to claim 12.

24. The method of denoising a signal according to claim 22, wherein at least one of the one or more relay nodes comprises a processor configured to execute the method of denoising a signal according to claim 12.

25. The method of denoising a signal according to claim 23, wherein at least one of the one or more relay nodes comprises a processor configured to execute the method of denoising a signal according to claim 12.

26. The method of denoising a signal according to claim 12, further comprising acquiring the signal using a sensor.

27. The method of denoising a signal according to claim 12, wherein the sensor is selected from a group consisting of acceleration sensors, gyroscopes, seismometers, electrodes, light detectors and receivers.

28. The method of denoising a signal according to claim 12, wherein the signal is from a scan of a spectroscopic image, and wherein prior to acquiring another scan, a processor executing the method of denoising a signal according to claim 12.

29. The method of denoising a signal according to claim 28, further comprising:
determining a signal to noise ratio in the denoised signal;
comparing the determined signal to noise ratio with a threshold; and
controlling the scanning based on the comparison.

30. The method of denoising a signal according to claim 29, wherein when the determined signal to noise ratio is less than the threshold, the controlling comprises causing an execution of a scan on a different region.

* * * * *